(12) United States Patent
Umemoto

(10) Patent No.: US 6,737,193 B2
(45) Date of Patent: May 18, 2004

(54) TETRAKETOPIPERAZINE UNIT-CONTAINING COMPOUND AS AN ACTIVE MATERIAL IN BATTERIES

(75) Inventor: Teruo Umemoto, Westminster, CO (US)

(73) Assignee: IM&T Research, Inc., Denver, CO (US)

( * ) Notice: Subject to any disclaimer, the term of this patent is extended or adjusted under 35 U.S.C. 154(b) by 31 days.

(21) Appl. No.: 10/028,064

(22) Filed: Dec. 20, 2001

(65) Prior Publication Data

US 2003/0148188 A1 Aug. 7, 2003

(51) Int. Cl.$^7$ ................................................ H01M 4/60
(52) U.S. Cl. ........................ 429/212; 429/209; 429/247; 429/232; 429/233; 429/217
(58) Field of Search ................................ 429/212, 209, 429/247, 232, 233, 217

(56) References Cited

U.S. PATENT DOCUMENTS

| | | | |
|---|---|---|---|
| 3,654,278 A | 4/1972 | Terenbaum | 260/268 |
| 5,460,905 A | 10/1995 | Skotheim | 429/213 |
| 6,201,071 B1 | 3/2001 | Miura et al. | 525/410 |
| 6,245,458 B1 | 6/2001 | Sotomura | 429/213 |
| 6,268,087 B1 | 7/2001 | Kim et al. | 429/231.95 |

OTHER PUBLICATIONS

J. Th. Bornwater, Rec. D. Trav. Chim., vol. 31, pp 129–131 (1912) (no abstract or interpretation).
"The Reaction of Oxalyl Chloride With Amine Hydrochlorides", J. Org. Chem. 1959, vol. 24, pp 1580–1581.
"Rechargeable Polypyrrole/Lithium Cells", Synthetic Metals, 18 (1987) pp 259–264.
"De Mouilpied and Rule: Tetraketopiperazine", J. Chem. Sec. 91, 176 (1907).
Analytica Chimica Acta, 87 (1976) 37–50, Electrochemical Reduction of Tetraketopiperazine.
"Electrochemically Active Polymers for Rechargeable Batteries", Chem. Rev. 1997, 97, 207–281.
"The Kinetics and Cyclability of Various Types of Polyacetylene Electrodes in Nonacueous Lithium Cells", J. Electrochem. Soc., 1984, pp 2761–2767.
"Polyacetylene and Polyphenylene as Anode Materials for Nonaqueous Secondary Batteries", J. Electrochem. Soc., 1987, pp 1529–1534.
"Ion Rechargeable Batteries Using Synthetic Organic Polymers", Synthetic Metals, 55–57 (1993) 3611–3616.
"Rechargeable Thin Film Batteries of Polypyrrole and Polyaniline", J. of App. Electrochem. 22 (1992) 738–742.
"Characteristics of Electrochemically Synthesized Polymer Electrodes in Lithium Cells", Electrochimica Acta. vol. 31, No. 12, pp. 1597–1600, 1986.
"Studies of Porous Polyacenic Semiconductors Toward Application", Synthetic Me tals, 38 (1990) 177–184.
"Protein Backbone Modification by Novel $C^\alpha$–C Side–Chain Scission", J. Am. Chem. Soc. 1994, 116, 6545–6557.
"The Polyfluorenes: A Family of Versatile Electroactive Polymers", New J. of Chem., vol. 11, N° 6–1987.
"Electrochemical Doping of Poly–(p–phenylene) with Application to Organic Batteries", J. Chem. Soc., Chem. Commun., 1982.
"Electrifying Plastics", Chem. & Eng. News, pp. 4–5, Oct. 16, 2000.
"Dimercaptan–polyaniline composite electrodes for lithium batteries with high energy density", Nature, vol. 373, Feb. 16, 1995.

*Primary Examiner*—Laura Weiner
(74) *Attorney, Agent, or Firm*—Dorsey & Whitney LLP

(57) ABSTRACT

Compounds containing at least one tetraketopiperazine-1,4-diyl unit are disclosed as active materials in the positive electrodes of batteries. Novel methods for preparing the tetraketopiperazine unit-containing compounds include: (i) reacting an oxalyl halide and an oxamide, and adding water or an aqueous alkali solution to the reaction mixture, (ii) reacting an oxalyl halide and a silylamine, (iii) reacting an oximidyl halide and an amine, (iv) reacting an oxalyl halide and a silylamine, and reacting with an amine, (v) reacting an oxalyl halide and a dioxamide, (vi) reacting an oximidyl halide and a diamine, and (vii) reacting an oxalyl halide and a silylamine, and reacting with a diamine. A novel method for preparing an oximidyl halide is also disclosed.

28 Claims, 3 Drawing Sheets

TETRAKETOPIPERAZINE UNIT-CONTAINING COMPOUND AS AN ACTIVE MATERIAL IN BATTERIES

FIELD OF THE INVENTION

The invention relates generally to a use of tetraketopiperazine unit-containing compounds as active ingredients in the positive electrodes of batteries and to methods for preparing the tetraketopiperazine unit-containing compounds.

BACKGROUND OF THE INVENTION

Batteries play an important role within industrialized society. It is estimated that on average ten batteries are used by every person in the United States every year. The economic and environmental impact of this usage is staggering and represents a major point of interest for those in and outside the art.

A battery, in general, is an electrochemical device that generates electric current by converting chemical energy to electrical energy. The essential components of a battery include the positive and negative electrode, a separating medium and an electrolyte. In general, chemically active materials at the negative electrode are oxidized to release electrons which travel to the positive electrode, creating a useable current, where they reduce chemically active materials at the positive electrode. The separating medium keeps the two electrodes insulated from each other, while the electrolyte maintains the oxidizing environment at the negative electrode and the reducing environment at the positive electrode.

Presently, most batteries rely upon chemically active materials that contain metal oxide compounds, due to their excellent oxidizing and reducing capabilities. The metal oxide compounds typically contain manganese, cobalt, nickel, lead, silver, mercury, and the like. Unfortunately, especially in relation to non-rechargeable batteries, or primary batteries, the use of metal oxides represents a large scale environmental problem, where production and disposal of the batteries may result in the release of heavy metals into the environment.

For at least these reasons, there has been an emphasis on developing active materials that limit the use of metal oxides in the electrodes, and in particular, developing organic materials to replace the metal oxides. However, organic materials have proven expensive to produce in the large quantities required for use in battery applications, and have failed to show the requisite electric capacity needed in most battery applications. *Synthesis Metals*, 1987, 259–264. Against this backdrop the present invention has been developed.

SUMMARY OF THE INVENTION

Embodiments of the present invention are directed at novel uses of a compound having at least one tetraketopiperazine-1,4-diyl unit, as represented by formula (1), as an active material in the positive electrodes of batteries.

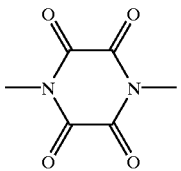

Formula (1)

Preferable embodiments of the present invention are directed at novel uses of the compound, where the compound has one or two tetraketopiperazine-1,4-diyl units as the active material in the positive electrodes of batteries.

Other embodiments of the present invention are directed at novel uses of a -mono(tetraketopiperazine) compound and di(tetraketopiperazine) compound represented by formulas (1-1) and (1-2), respectively, as active materials in the positive electrodes of batteries.

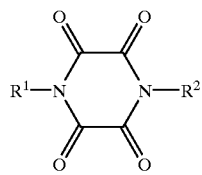

Formula (1-1)

$R^1$ and $R^2$ are independently a hydrogen atom or a substituted or unsubstituted alkyl or aryl group.

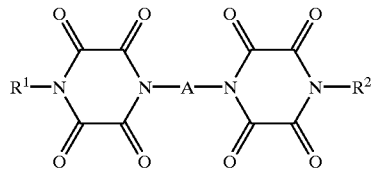

Formula (1-2)

$R^1$ and $R^2$ are defined as above and A is a substituted or unsubstituted alkylene or arylene group.

Method A

Other embodiments of the present invention are directed at methods for preparing mono(tetraketopiperazine) compound as represented by formula (1-1) above, by reacting an oxalyl halide represented by formula (2) and an oxamide represented by formula (3), and adding water or an aqueous alkali solution to the reaction mixture. The addition of water or an aqueous alkali solution provides for a substantial increase in the yield of the tetraketopiperazine compound.

$$X^1\text{—COCO—}X^2 \qquad \text{Formula (2)}$$

The $X^1$ and $X^2$ are independently a halogen atom.

$$R^1\text{—NH—COCO—NH—}R^2 \qquad \text{Formula (3)}$$

The $R^1$ and $R^2$ are defined as above.

Method B

In another embodiment of the present invention, the mono(tetraketopiperazine) compound represented by formula (1-1) above is prepared by reacting an oxalyl halide represented by formula (2) above and a silylamine represented by formula (4).

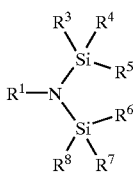

Formula (4)

$R^1$ is defined as above and $R^3$, $R^4$, $R^5$, $R^6$, $R^7$ and $R^8$ are independently a substituted or unsubstituted alkyl or aryl group.

Method C

In another embodiment of the present invention, the mono(tetraketopiperazine) compound represented by formula (1-1) above is prepared by reacting an oximidyl halide represented by formula (5) and an amine represented by formula (6).

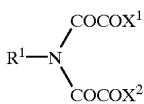

Formula (5)

$R^1$, $X^1$, and $X^2$ are defined as above.

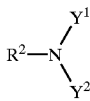

Formula (6)

$R^2$ is defined as above, and $Y^1$ and $Y^2$ are independently a hydrogen atom, $SiR^3R^4R^5$, or $SiR^6R^7R^8$, in which $R^3$, $R^4$, $R^5$, $R^6$, $R^7$ and $R^8$ are independently a substituted or unsubstituted alkyl or aryl group.

Method D

In another embodiment of the present invention, the mono(tetraketopiperazine) compound represented by formula (1-1) above is prepared by reacting an oxalyl halide represented by formula (2) above and a silylamine represented by formula (4) above, and reacting with an amine represented by formula (6) above.

Method E

In another embodiment of the present invention, a di(tetraketopiperazine) compound represented by formula (1-2) above is prepared by reacting an oxalyl halide represented by formula (2) above and a dioxamide represented by formula (7), and, preferably, adding water or an aqueous alkali solution to the reaction mixture.

$R^1$—NH—COCO—NH—A—NH—COCO—NH—$R^2$  Formula (7)

$R^1$, $R^2$ and A are defined as above.

Method F

In another embodiment of the present invention, the di(tetraketopiperazine) compound represented by formula (1-2) above is prepared by reacting an oximidyl halide represented by formula (5) above and a diamine represented by formula (8).

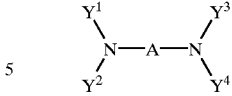

Formula (8)

A is defined as above, and $Y^1$, $Y^2$, $Y^3$, and $Y^4$ are independently a hydrogen atom, $SiR^3R^4R^5$, $SiR^6R^7R^8$, $SiR^9R^{10}R^{11}$, or $SiR^{12}R^{13}R^{14}$, in which $R^3$, $R^4$, $R^5$, $R^6$, $R^7$, $R^8$, $R^9$, $R^{10}$, $R^{11}$, $R^{12}$, $R^{13}$ and $R^{14}$ are independently a substituted or unsubstituted alkyl or aryl group.

Method G

In another embodiment of the present invention, the di(tetraketopiperazine) compound represented by formula (1-2) above is prepared by reacting an oxalyl halide represented by formula (2) above and a silylamine represented by formula (4) above, and reacting with a diamine represented by formula (8) above.

Finally, in another embodiment of the present invention, oximidyl halide represented by formula (5) above is prepared by reacting an oxalyl halide represented by formula (2) above with a silylamine represented by formula (4) above. The oximidyl halide of formula (5) above is an important intermediate for preparing the mono- and di(tetraketopiperazine) compounds represented by formulas (1-1) and (1-2) above.

Other embodiments of the present invention relates to new compounds produced by the methods of the present invention, which include N,N'-diethyl-2,3,5,6-tetraketopiperazine, N-alkyl-N'-aryl-2,3,5,6-tetraketopiperazine, and the di(tetraketopiperazine) compounds represented by formula (1-2) above.

These and various other features as well as advantages which characterize the invention will be apparent from a reading of the following detailed description and a review of the appended claims.

BRIEF DESCRIPTION OF THE DRAWINGS

FIG. 1 is a partial cross-sectional view of a Li battery utilizing a tetraketopiperazine unit-containing compound as the active material in the positive electrode in accordance with one embodiment of the present invention.

FIG. 2 illustrates a discharge curve at constant current of a Li battery utilizing N,N'-dimethyl-2,3,5,6-tetraketopiperazine as the active material in the positive electrode.

FIG. 3 illustrates a discharge curve at constant current of a Li battery utilizing di(tetraketopiperazine) compound represented by formula (1-2), $R^1$=$R^2$=$CH_3$, A=$(CH_2)_2$, as the active material in the positive electrode.

DETAILED DESCRIPTION OF THE INVENTION

Figure 1:
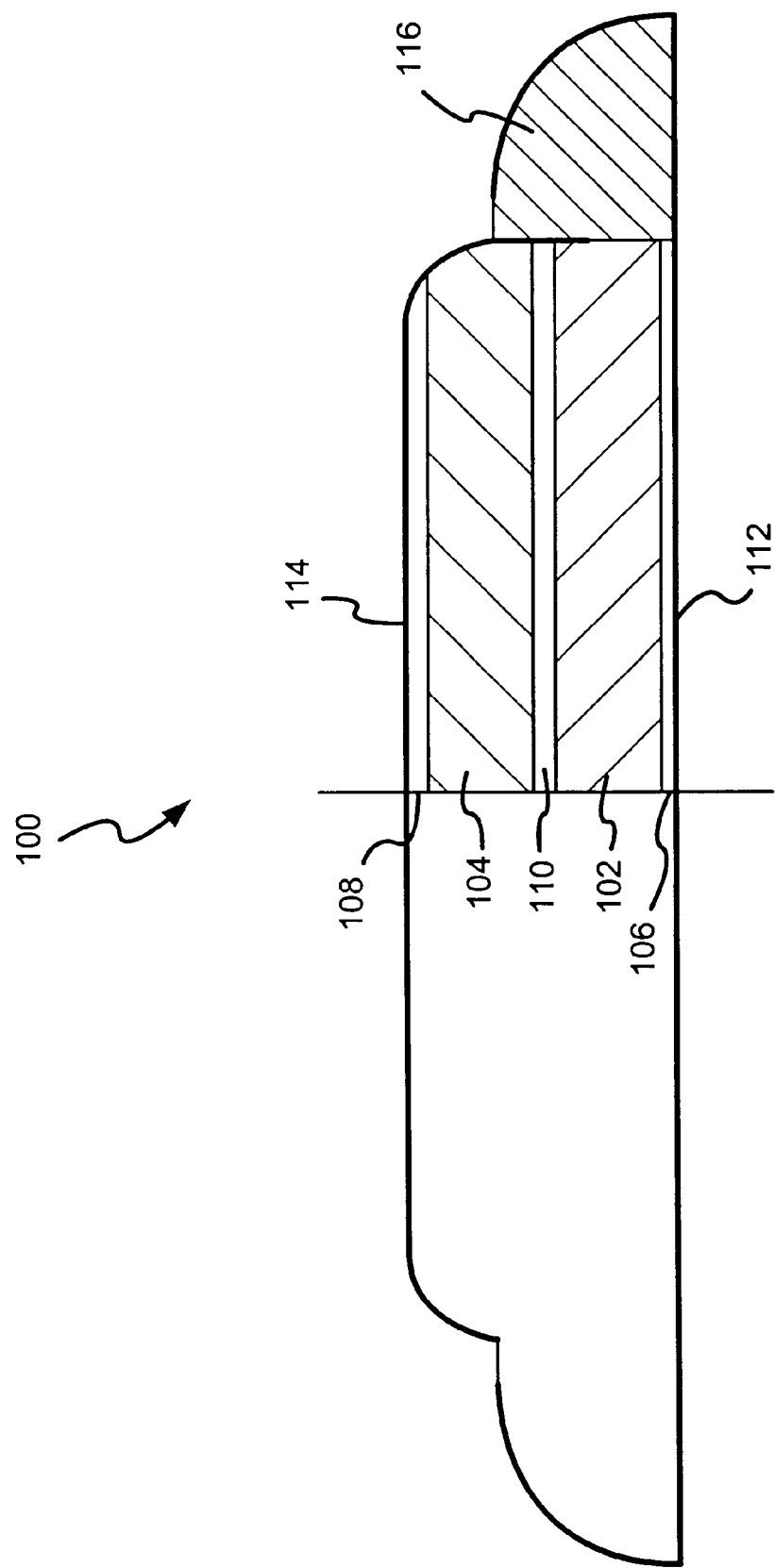
FIG. 1

Embodiments of the present invention are based upon the fact that a compound having at least one tetraketopiperazine-1,4-diyl unit, represented by formula (1), can be employed as an active material in the positive electrode of either a primary or secondary battery. In addition, embodiments of the present invention are directed at novel methods for preparing the compounds having at least one tetraketopiperazine-1,4-diyl unit.

Definitions

The following definitions are provided to facilitate understanding of certain terms used frequently herein and are not meant to limit the scope of the present disclosure.

"Compound" as used in this invention refers to a substance formed by the combination of elements in fixed proportions. The formation of a compound involves a chemical reaction; i.e., there is a change in the configuration of the valence electrons of the atoms. Compounds, unlike mixtures, cannot be separated by physical means.

"A compound having at least one tetraketopiperazine-1,4-diyl unit" refers to a compound whose structural formula comprises at least one tetraketopiperazine-1,4-diyl unit. Preferably these compounds have at least 20% or more, more preferably 40% or more, and most preferably 60% or more of tetraketopiperazine-1,4-diyl units by weight.

"A tetraketopiperazine-1,4-diyl unit-containing compound" refers to a compound whose structural formula comprises at least one tetraketopiperazine-1,4-diyl unit.

"The polymeric compound" used in "the polymeric compounds have about 15 or more tetraketopiperazine-1,4-diyl units" refers to the compound whose structural formula comprises about 15 or more tetraketopiperazine-1,4-diyl units.

"The oligomeric compound" used in "the oligomeric compounds have 4 to about 15 tetraketopiperazine-1,4-diyl units" refers to the compound whose structural formula comprises 4 to about 15 tetraketopiperazine-1,4-diyl units.

"The trimeric compound" used in "the trimeric compounds have three tetraketopiperazine-1,4-diyl units" refers to the compound whose structural formula comprises three tetraketopiperazine-1,4-diyl units.

"The dimeric compound" used in "the dimeric compounds have tetraketopiperazine-1,4-diyl units" refers to the compound whose structural formula comprises two tetraketopiperazine-1,4-diyl units.

"The monomeric compound" used in "the monomeric compounds have one tetraketopiperazine-1,4-diyl unit" refers to the compound whose structural formula comprises one tetraketopiperazine-1,4-diyl unit.

Compounds Having at Least One Tetraketopiperazine-1,4-diyl Unit Represented by Formula (1) as an Active Material in a Positive Electrode Embodiments of the present invention are directed at novel uses for compounds having at least one tetraketopiperazine-1,4-diyl unit as represented by formula (1) as an active material or an ingredient of an active material in the positive electrodes of batteries, e.g., primary or secondary batteries.

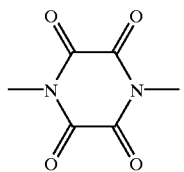

Formula (1)

In order to obtain a high electric capacity, the tetraketopiperazine-1,4-diyl unit content of the compound is preferably 20% or more, more preferably 40% or more, and furthermore preferably 60% or more by weight. The compound having at least one tetraketopiperazine-1,4-diyl unit may be any type of compound, for example, such as polymeric, oligomeric, trimeric, dimeric, or monomeric compounds. The polymeric compounds have about 15 or more tetraketopiperazine-1,4-diyl units, the oligomeric compounds have 4 to about 15 tetraketopiperazine-1,4-diyl units, the trimeric compounds have three tetraketopiperazine-1,4-diyl units, the dimeric compounds have two tetraketopiperazine-1,4-diyl units, and the monomeric compounds have one tetraketopiperazine-1,4-diyl unit in the structural formula.

The portion other than the tetraketopiperazine-1,4-diyl unit in the structural formula of a compound of the present invention may be any composition that does not prevent the activity of the tetraketopiperazine-1,4-diyl unit as an active material in a positive electrode. The portion may be composed of any elements such as, preferably, carbon (C), hydrogen (H), oxygen (O), nitrogen (N), halogen (F, Cl, Br, and/or I), sulfur (S), silicon (Si), boron (B), aluminum (Al), phosphate (P), and/or metals (preferably, alkali metals such as Li, Na, and K, and/or alkali earth metals such as Mg and Ca). Preferable tetraketopiperazine-1,4-diyl unit-containing compounds are the monomeric compounds or the dimeric compounds based on the relative ease of their production.

As exemplified in FIG. 1, a battery 100 is fundamentally composed of a positive electrode 102, a negative electrode 104, and an electrolytic solution. When required, each of the electrodes 102 and 104 may have a current collector 106 and 108 and a separator 110 between electrodes 102 and 104. A positive electrode cap 112 and negative electrode cap 114 encase the respective electrodes and a gasket 116 seals the battery.

In use, the compound having at least one tetraketopiperazine-1,4-diyl unit represented by formula (1) is the active material or the active ingredient of the positive electrode where it accepts electrons generated at the negative electrodes As shown in Scheme 1, the compound having at least one tetraketopiperazine-1,4-diyl unit represented by formula (1) may be stepwise reduced to the compounds having units shown by formulas (1a) and (1b) by two electrons per tetraketopiperazine-1,4-diyl unit.

Scheme 1

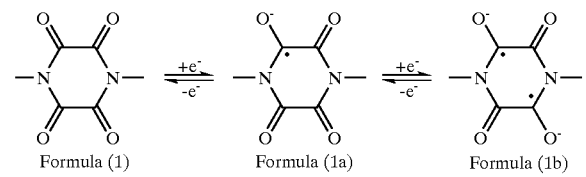

Formula (1)   Formula (1a)   Formula (1b)

As such, a compound having one tetraketopiperazine-1,4-diyl unit represented by formula (1) may be stepwise reduced by two electrons to the corresponding compounds having units shown by formula (1a) and formula (1b), and a compound having two tetraketopiperazine-1,4-diyl units is reduced by four electrons. A compound having n number of tetraketopiperazine-1,4-diyl units is reduced by 2n electrons. Importantly, it should be noted that the reaction at the positive electrode is reversible, making the tetraketopiperazine unit-containing compounds a suitable active material for secondary batteries as well.

In an embodiment of the present invention, the compound having at least one tetraketopiperazine-1,4-diyl unit (formula (1)) is pulverized and pressed onto a current collector. Note that other forms, for example painting, of the tetraketopiperazine unit-containing compound are envisioned to be within the scope of the present invention, as long as the material is in electrical communication with the current collector and is generally encased within the positive electrode. For purposes of this invention, any number of current collectors may be used, for example, a plate or thin layer of various carbonaceous materials, such as carbon fiber, pitch, tar, carbon blacks such as acetylene black, graphites, such as natural graphite, artificial graphite, and kish graphite. The current collector may also be a plate, a foil, a thin layer, a net, a mesh, a punching metal (foamed metal), a metal fiber net, or the like, which are made of metals such as platinum, gold, nickel, stainless steel, iron, copper, aluminum, and the like. Preferable current collectors for use with this invention include, but are not limited to, a plate and a thin layer of carbonaceous materials and a plate, thin layer, net, and mesh of gold, nickel, stainless steel, and iron.

Scheme 2 shows two half-reactions and a total reaction of a battery using one embodiment of the present invention. The tetraketopiperazine-1,4-diyl unit (formula (1)) is an active unit of the material at the positive electrode and lithium at the negative electrode, one possible total reaction of the battery is also shown with the corresponding half reactions.

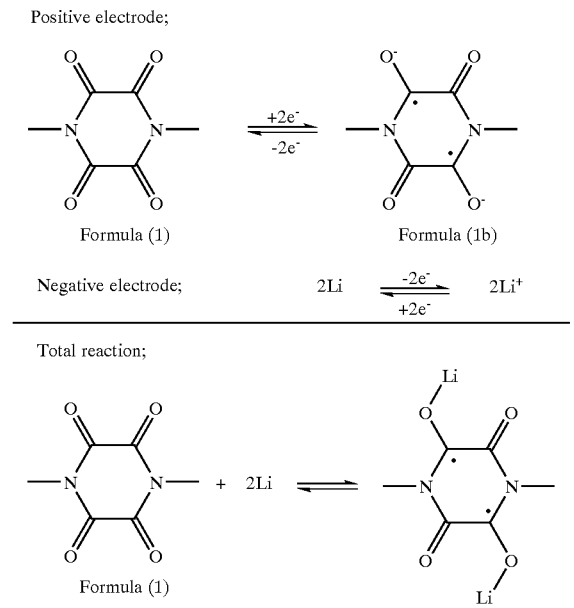

In another embodiment of the present invention, the active material at the positive electrode is a mixture of a compound having at least one tetraketopiperazine-1,4-diyl unit represented by formula (1) and an electroconductive agent for enhancing the flow of electrons to and from the tetraketopiperazine unit-containing compound. There are a number of possible electroconductive agents that may be employed with the present invention, including, but not limited to, various carbonaceous materials such as carbon fiber, pitch, tar, carbon blacks, such as acetylene black, and graphites, such as artificial graphite or kish graphite; metal powders, such as nickel powder and platinum powder; and various fine metal fibers. Preferable electroconductive agents for use with the present invention include carbon blacks such as acetylene black, graphites, and the like.

In another embodiment of the present invention, the active material of the positive electrode is a mixture of a compound having at least one tetraketopiperiazine-1,4-diyl unit represented by formula (1) and a binder for facilitating the tetraketopiperazine unit-containing compound remaining on the positive electrode. There are a number of possible binders that may be employed with the present invention, including, but not limited to, poly(tetrafluoroethylene), poly (vinylidene fluoride), a solution of poly(vinylidene fluoride) in N,N-dimethylformamide, carboxymethylcellulose, poly (methyl acrylate), poly(methyl methacrylate), poly(ethyl acrylate), poly(ethyl methacrylate), poly(acrylonitorile), and the like. Preferable binding agents for use with the present invention include poly(tetrafluoroethylene), poly(vinylidene fluoride), a solution of poly(vinylidene fluoride) in N,N-dimethylformamide, poly(methyl acrylate), poly(methyl methacrylate), and poly(acrylonitrile).

In another embodiment of the present invention, the active material at the positive electrode is a-mixture of a compound having at least one tetraketopiperazine-1,4-diyl unit of formula (1) and an electrolyte or aprotic and/or protic polar solvent to keep the smooth electrochemical reaction at the positive electrode. Electrolytes and polar solvents for use in this embodiment are discussed in greater detail below.

In another embodiment of the present invention, the active material at the positive electrode is a mixture of a compound having at least one tetraketopiperazine-1,4-diyl unit represented by formula (1) and a more traditional positive electrode active material, i.e., other materials that accept electrons or are reduced at the positive electrode. Examples include; metal oxides such as $MnO_2$, NiOOH, $LiMn_2O_3$, $LiMn_2O_3$, $LiCoO_2$, $LiNiO_2$, $PbO_2$, AgO, $Ag_2O$, $Ag_2CrO_4$, $AgV_4O_{11}$, HgO, $Cu_4O(PO_4)_2$, CuO, $Bi_2O_3$, $Bi_2Pb_2O_5$, $MoO_3$, and $V_2O_5$; metal sulfides such as $FeS_2$, CuS, and $Ni_3S_2$; metal halides such as AgCl, $CuCl_2$, and $CuF_2$; non-metal inorganic compounds such as $I_2$, $SO_2$, $SOCl_2$, $SO_2Cl_2$; carbon monofluoride $[(CF)_n]$; organic polymers such as polyaniline, polypyrrole, and polythiophene; and the like. Note that the materials may be mixtures of the above traditional materials. Also note that mixing the metal oxide, metal sulfide, or metal halide with the tetraketopiperazine unit-containing compound leads to the reduction of the amount of metal compound needed at the positive electrode, and therefore would represent a smaller environmental risk than "standard" batteries.

Finally, active materials at the positive electrode may include compounds having at least one tetraketopiperazine-1,4-diyl unit represented by formula (1) mixed with more than one of the above discussed additions at the same time, including the electroconductive agent, binder, electrolyte, polar solvent, and known active materials. Therefore, for example, the positive electrode may entail the tetraketopiperazine unit-containing compound mixed with an electroconductive agent and binder. In one preferred embodiment, 20–97% (by wt) of the tetraketopiperazine-1,4-diyl unit-containing compound, 2 to 70% acetylene black and 1 to 25% binder are combined at the positive electrode.

Negative electrodes for use with the present invention may include alkali metals, such as lithium, sodium, and potassium; alkali earth metals, such as magnesium and calcium; transition metals, such as zinc; alloys containing any of the above, such as lithium alloys such as lithium-aluminum; and materials, such as carbonaceous materials or polymers, such as poly(acene), doped with metal ions, such as lithium ion, all of which are known within the art.

Electrolytes for use with the present invention include ones typically used within the art irrespective of being a liquid, gel, or solid. Preferable liquid electrolytes for use in the present invention include, but are not limited to, aprotic and protic polar solvents, in which $LiPF_6$, $NaPF_6$, $KPF_6$, $LiPF_3(C_2F_5)_3$, $LiAsF_6$, $LiSbF_6$, $LiBF_4$, $NaBF_4$, $KBF_4$, $LiClO_4$, $CF_3SO_3Li$, $(CF_3SO_2)_2NLi$, $(C_2F_5SO_2)_2NLi$, sodium chloride, sulfuric acid, phosphoric acid, hydrogen chloride, or the like is dissolved. Aprotic solvents include, but are not limited to, carbonic esters, examples of which include propylene carbonate, ethylene carbonate, butylene carbonate, dimethyl carbonate, diethyl carbonate, ethyl methyl carbonate, trifluoropropylene carbonate, bis(2,2,2- trifluoroethyl) carbonate, and methyl (2,2,2-trifluoroethyl) carbonate; malonates, such as dimethyl 2,2-difluoromalonate; nitriles, such as acetonitrile, propionitrile, and benzonitrile; aliphatic esters, such as methyl formate, ethyl formate, methyl acetate, ethyl acetate, and methyl propionate; lactones, such as r-butyrolactone, and r-valerolactone; ethers, such as tetrahydrofuran, 2-methyltetrahydrofuran, 1,3-dioxolane, 4-methyldioxolane, diethyl ether, dimethoxyethane, and dioxane; sulfoxides, such as dimethylsulfoxide; sulfolanes, such as sulfolane and methylsulfolane; amides, such as N,N-dimethylformamide, N-methylpyrrolidinone, and N-methyloxazolidinone; ionic liquids, such as 1-ethyl-3-methyl-1H-imidazolium triflate, 1-ethyl-3-methyl-1H-imidazolium tetrafluoroborate, and 1-ethyl-3-methyl-1H-imidazolium bis(trifluoromethanesulfonyl)amide, and 1-butyl-3-methyllimidazolium hexafluorophosphate. Protic polar solvents include, but are not limited to, water; alcohols such as methanol ethanol, propanol, isopropanol, butanol, isobutanol, and tert-butanol; glycols such as ethylene glycol, propylene glycol; glycerol; and the like. Gel electrolytes include, but are not limited to, gel electrolyte comprising polymer, a protic or aprotic polar solvent, and an electrolyte, such as poly(ethylene oxide)/propylene carbonate/LiClO$_4$, poly(vinylidene fluoride-co-12% hexafluoropropylene)/ ethylene carbonate-propylene carbonate/LiPF$_6$, poly (acrylonitrile)/propylene carbonate-ethylene carbonate/LiN (SO$_2$CF$_3$)$_2$, poly(methyl methacrylate)/γ-butyrolactone/ LiBF$_4$, polysulfone/propylene carbonate/LiClO$_4$, and the like. Solid electrolytes include, but are not limited to, CF$_3$SO$_3$Li, LiBF$_4$, LiAsF$_6$, LiSbF$_6$, LiPF$_6$, (CF$_3$SO$_2$)$_2$NLi, (C$_2$F$_5$SO$_2$)$_2$NLi, poly(ethylene oxide)/LiClO$_4$, poly (ethylene oxide)/NaI, poly(ethylene oxide)/CF$_3$SO$_3$Li, poly (propylene oxide)/CF$_3$SO$_3$Li, and the like. For high energy and high electric current, the liquid electrolytes are preferable, which include aprotic polar solvents such as carbonic esters, aliphatic esters, lactones, ethers and ionic liquids, in which the metal salts such as lithium salts are dissolved. Note that the above liquid electrolytes may comprise mixtures of the above solvents, with preferred mixtures including carbonic esters, aliphatic esters, lactones, ethers, and ionic liquids.

The separator is not necessary when an insulator layer or film as the separating medium can be spontaneously made between the positive and negative electrode by the reaction of a component(s) of materials contained in the battery with the electrode materials on the surface of either or both electrodes. If necessary, a separator material appropriate for use with the present invention may include, but is not limited to, glass fibers, woven fabrics, non-woven fabrics, polyesters, polypropylene, and polyamides.

The actual assembly of a battery, for example using materials of the present invention, is well known in the art.

Mono- and Di(tetraketopiperazine) Compounds Represented by Formulas (1-1) and (1-2) are Active Material in a Positive Electrode In a preferred embodiment of the present invention, an active material or ingredient of the active material in a positive electrode of a battery, e.g., primary or secondary battery, is a compound having at least one tetraketopiperazine-1,4-diyl unit (formula (1)) that is further defined as a mono- and di(tetraketopiperazine) compound represented by formulas (1-1) and (1-2), respectively, shown below:

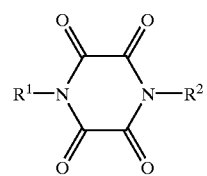

Formula (1-1)

$R^1$ and $R^2$ are independently a hydrogen atom or a substituted or unsubstituted alkyl or aryl group.

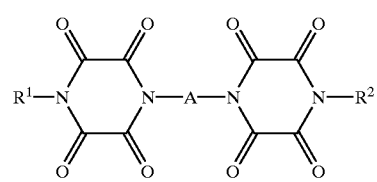

Formula (1-2)

$R^1$ and $R^2$ are defined as above, and A is a substituted or unsubstituted alkylene or arylene group.

The alkyl group of $R^1$ or $R^2$ is preferably an alkyl group having from 1 to 10 carbon atoms which is unsubstituted or substituted with one or more substituents selected from the group consisting of a halogen atom, an aryl group, an alkoxy group, and an aryloxy group. Preferable substituted or unsubstituted alkyl groups for $R^1$ or $R^2$ of formulas (1-1) and (1-2), are, for example, methyl, benzyl, ethyl, 1,1,1-trifluoroethyl, phenylethyl, methoxyethyl, phenoxyethyl, propyl, isopropyl, cyclopropyl, methoxypropyl, butyl, isobutyl, t-butyl, pentyl, cyclopentyl, hexyl, cyclohexyl, heptyl, octyl, nonyl, and decyl. More preferably, the alkyl group of $R^1$ or $R^2$ is an alkyl group having 1 to 4 carbon atoms which is unsubstituted or substituted with one or more substituents selected from the group shown above.

The aryl group of $R^1$ or $R^2$ is preferably an aryl group having 6 to 10 carbon atoms which is unsubstituted or substituted with one or more substituents selected from the group consisting of an alkyl group, a halogen atom, an acyl group, a nitro group, a cyano group, an alkoxy group, an acylamino group, an alkylthio group, and an alkanesulfonyl group. As the preferable substituted or unsubstituted aryl group consisting of 6 to 10 carbon atoms for $R^1$ or $R^2$, there are, for example, phenyl, ortho(o)-, meta(m)-, or para(p)-tolyl, o-, m-, or p-fluorophenyl, chlorophenyl, bromophenyl, iodophenyl, methoxyphenyl, acetylphenyl, nitrophenyl, cyanophenyl, (acetylamino)phenyl, (methylthio)phenyl, (methanesulfonyl)phenyl, xylyl, difluorophenyl, pentafluorophenyl, and 1- or 2-naphthyl. More preferably, the aryl group of $R^1$ or $R^2$ is an aryl group having 6 to 8 carbon atoms which is unsubstituted or substituted with one or more substituents selected from the group shown above.

Preferably, the alkylene group of A is an alkylene group having 1 to 10 carbon atoms which is unsubstituted or substituted with one or more substituents selected from the group consisting of an alkyl group, a halogen atom, an aryl group, an alkoxy group, and aryloxy group. As the preferable substituted or unsubstituted alkylene group consisting 1–10 carbon atoms for A, there are, for example, CH$_2$, CH$_2$CH$_2$, CH(CH$_3$)CH$_2$, CH(C$_6$H$_5$)CH$_2$, CH$_2$CH$_2$CH$_2$, CH$_2$CF$_2$CH$_2$, CH$_2$CH$_2$(OCH$_3$)CH$_2$, CH$_2$CH$_2$(OC$_6$H$_5$)CH$_2$, CH$_2$(CH$_2$)$_2$CH$_2$, CH$_2$(CF$_2$)$_2$CH$_2$, CH$_2$(CH$_2$)$_3$CH$_2$, CH$_2$ (CF$_2$)$_3$CH$_2$, CH$_2$(CH$_2$)$_4$CH$_2$, CH$_2$(CF$_2$)$_4$CH$_2$, CH$_2$(CH$_2$)$_5$ CH$_2$, CH$_2$(CH$_2$)$_6$CH$_2$, CH$_2$(CH$_2$)$_7$CH$_2$, and CH$_2$(CH$_2$)$_8$ CH$_2$. More preferably, the alkylene group of A is an alkylene group having 1 to 4 carbon atoms which is unsubstituted or substituted with one or more substituents selected from the group shown above.

Preferably, the arylene group of A is an arylene group having 6 to 10 carbon atoms which is unsubstituted or substituted with one or more substituents selected from the group consisting of an alkyl group, a halogen atom, an acyl group, a nitro group, a cyano group, an alkoxy group, an acylamino group, an alkylthio group, and an alkanesulfonyl group. As the preferable substituted or unsubstituted arylene group consisting of 6 to 10 carbon atoms for A, there are, for example, o-phenylene, m-phenylene, p-phenylene, methyl-o, m, or p-phenylene, dimethyl-o, m, or p-phenylene, ethyl-o, m, or p-phenylene, propyl-o, m, or p-phenylene, butyl-o, m, or p-phenylene, fluoro-o, m, or p-phenylene, difluoro-o, m, or p-phenylene, trifluoro-o, m, or p-phenylene, tetrafluoro-o, m, or p-phenylene, chloro-o, m, or p-phenylene, nitro-o, m, or p-phenylene, cyano-o, m, or p-phenylene, methoxy-o, m, or p-phenylene, acetyl-o, m, or p-phenylene, methylthio-o, m, or p-phenylene, methanesulfonyl-o, m, or p-phenylene. More preferably, the arylene group of A is an arylene group having 6 to 8 carbon atoms which is unsubstituted or substituted with one or more substituents selected from the group shown above.

Process for Preparing Mono(tetraketopiperazine) Compounds Represented by Formula (1-1)

2,3,5,6-Tetraketopiperazine [*Journal of the Chemical Society*, Vol. 91, p.p. 176–183 (1907); *Analitica Chimica Acta*, Vol. 87, p.p. 37050 (1976)], N,N'-dimethyl-2,3,5,6-tetraketopiperazine [*Rec. D. Trav. Chim.*, Vol. 31, p.p. 129–131 (1912)] and N,N'-diaryl-2,3,5,6-tetraketopiperazines in which the aryl groups are p-carbethoxyphenyl, p-tolyl, and p-bromophenyl [U.S. Pat. No. 3,654,278 (1972)] have been previously prepared, but methods for their preparation were not satisfactory from a viewpoint of yields, simplicity, and reproducibility of the processes.

The present invention of the processes was developed against these drawbacks.

Method A: The Reaction of Oxalyl Halide and Oxamide

One embodiment of the present invention relates to a process for preparing mono(tetraketopiperazine) compounds represented by formula (1-1) by reacting an oxalyl halide represented by formula (2) and an oxamide represented by formula (3) in an appropriate solvent, and adding either water or an aqueous alkali solution to the reaction mixture (see reaction scheme 3).

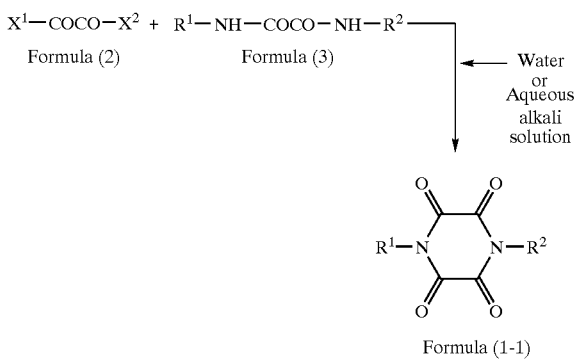

Scheme 3 (Method A)

Compounds

The term oxaly halide refers to any compound having a chemical formula as represented by formula (2), where $X^1$ and $X^2$ are independently a halogen atom such as fluorine, chlorine, bromine, and iodine, preferably a fluorine atom or chlorine atom, and most preferably a chlorine atom. A variety of oxalyl halide compounds may be employed in the present invention, including oxalyl fluoride (FCOCOF), oxalyl chloride (ClCOCOCl), oxalyl bromide (BrCOCOBr), oxalyl chloride fluoride (ClCOCOF), oxalyl bromide chloride (ClCOCOBr), oxalyl iodide (ICOCOI), and the like. The preferred oxalyl halide for the present invention is oxalyl chloride, due to its relative low cost.

The term oxamide refers to any compound having a chemical formula (3), where $R^1$ and $R^2$ are defined as above. Oxamides are commercially available, or easy to prepare according to technology well known in the art. Preferable oxamides employed in the present invention include: N,N'-dimethyloxamide, N-methyl-N'-phenyloxamide, N-methyl-N'-(o, m, or p-tolyl)oxamide, N-methyl-N'-(fluorophenyl) oxamide, N-methyl-N'-(chlorophenyl)oxamide, N-methyl-N'-(methoxyphenyl)oxamide, N-methyl-N'-(acetylphenyl) oxamide, N-methyl-N'-(nitrophenyl)oxamide, N-methyl-N'-[(acetylamino)phenyl]oxamide, N-methyl-N'-naphthyloxamide, N,N'-diethyloxamide, N-ethyl-N'-ethyl-N'-phenyloxamide, N-methyl-N'-ethyloxamide, N,N'-dipropyloxamide, N-propyl-N'-methyloxamide, N,N'-di(cyclopropyl)oxamide, N,N'-diisopropyloxamide, N,N'-dibutyloxamide, N,N'-diisobutyloxamide, N,N'-di-t-butyloxamide, N,N'-dipentyloxaminde, N,N'-di(cyclopentyl)oxamide, N,N'-dihexyloxamide, N,N'-di(cyclohexyl)oxamide, N,N'-dioctyloxamide, N,N'-didecyloxamide, N,N'-diphenyloxamide, N,N'-ditolyloxamide, N,N'-bis(fluorophenyl)oxamide, N,N'-bis(chlorophenyl)oxamide, N,N'-bis(acetylphenyl)oxamide, N,N'-bis(nitrophenyl)oxamide, N,N'-bis(cyanophenyl) oxamide, N,N'-bis(methoxyphenyl)oxamide, N,N'-bis(methylthiophenyl)oxamide, and N,N'-bis(methanesulfonyl) phenyl)oxamide. More preferably, the oxamides employed in the present invention are N,N'-dimethyloxamide, N,N'-diethyloxamide, N,N'-diphenyloxamide, N,N-ditolyloxamide, N,N'-bis(fluorophenyl)oxamide, N,N'-bis(nitrophenyl)oxamide, N-methyl-N'-phenyloxamide, N-methyl-N'-tolyloxamide, N-methyl-N'-(fluorophenyl) oxamide, and N-methyl-N'-(nitrophenyl)oxamide.

Examples of suitable solvents for use with the present invention include compounds having a nitrile group, for example, acetonitrile, propionitrile, and benzonitrile. The most preferred solvent for use with the present invention is acetonitrile due to its relative ease of procurement and low cost.

The term alkali in aqueous alkali solution refers to any compound that shows alkalinity in water. Preferable examples of alkalis include: hydroxides, such as metal hydroxides in which the metals are alkali metals, alkali earth metals, and transition metals, and ammonium hydroxides such as tetramethylammonium hydroxide, tetraethylammonium hydroxide, tetrabutylammonium hydroxide, benzyltrimethylammonium hydroxide and the like; ammonia; amines, such as methylamine, diethylamine, trimethylamine, ethylamine, diethylamine, triethylamine, propylamine, butylamine, aniline, and the like; pyridines, such as pyridine, methylpyridine, dimethylpyridine, trimethylpyridine, and the like; alkali metal and earth metal salts of carbonic acid, such as sodium carbonate, sodium bicarbonate, potassium carbonate, magnesium carbonate, calcium carbonate, and the like; alkali metal and alkali earth metal salts of carboxylic acids, such as sodium acetate, potassium acetate, magnesium acetate, and the like; alkali metal and alkali earth metal salts of phosphoric acid, such as sodium phosphate, potassium phosphate and the like. Note that the term alkali in aqueous alkali solution may refer to a mixture of any of the above compounds. Preferable alkali for the present invention include: alkali metal and alkali earth metal hydroxides, such as sodium hydroxide, potassium hydroxide, lithium hydroxide, rubidium hydroxide, cesium hydroxide, magnesium hydroxide, calcium hydroxide, barium hydroxide, and the like. Note that the concentration of the alkali in the aqueous alkali solution may vary, but is preferably between 2% by weight and the maximum concentration of the solvent used.

Use of an aqueous acid solution other than water or an aqueous alkali solution is included in the use of water in this invention, because a large amount of a hydrogen halide that has a strong acidic nature is formed by the reaction of the oxamide and the oxalyl halide as described below, and thus the added water becomes an aqueous acid solution.

The Process

An embodiment of the invention for producing the mono (tetraketopiperazine) compound represented by formula (1-1) is a process that comprises: mixing an oxamide represented by formula (3) and an oxalyl halide represented by formula (2) using a molar ratio of from 1:10 to 10:1, respectively, preferably from 1:2 to 2:1, and more preferable from 1:1.5 to 1.5:1. The reactants are mixed in solvent at between −50° C. and 200° C., and preferably between −20° C. and 150° C., and most preferably between 10° C. and 100° C. The reaction mixture is allowed to stir, and water or an aqueous alkali solution was added to the reaction mixture. Since the reaction time depends on the reaction conditions (temperature, molar ratio, solvent, and others), the reaction time may vary for each reaction.

The amount of water added to the reaction is from 1:10 to 1000:1 molar ratio, preferably from 1:5 to 100:1 molar ratio, more preferably from 1:2 to 10:1 molar ratio, of water: hydrogen halide formed by the reaction of the oxamide with the oxalyl halide. The amount of aqueous alkaline solution added to the reaction is from 1:100 to 100:1 molar ratio, preferably from 1:10 to 10:1 molar ratio, more preferably from 1:5 to 5:1 molar ratio, of the sum of alkali and water of the aqueous alkali solution: hydrogen halide formed by the reaction of the oxamide with the oxalyl halide.

The addition of water or an aqueous alkali solution to the reaction favors the forward reaction, i.e., formation of the mono(tetraketopiperazine) compound. One potential reaction scheme is illustrated in Scheme 4. The oxalyl halide represented by formula (2) reacts with the oxamide represented by formula (3) to give an intermediate represented by formula (1-1b), which results in two isomeric products, formula (1-1) and formula (1-1a), by two different intramolecular cyclization reactions, routes a and b. The isomer illustrated as formula (1-1) is thermally more stable than the isomer illustrated by formula (1-1a). Water and an aqueous alkali solution can greatly decrease or neutralize the acidity of hydrogen halides, $HX^1$ and $HX^2$, which are evolved from the reaction. Therefore, the addition of water or aqueous alkali solution to the reaction mixture may accelerate the formation of the thermally more stable isomer (formula (1-1)) by favoring route a, the reverse reaction of route b followed by route a, and/or the rearrangement (route c) of the less stable isomer formula (1-1a) to the more stable isomer formula (1-1).

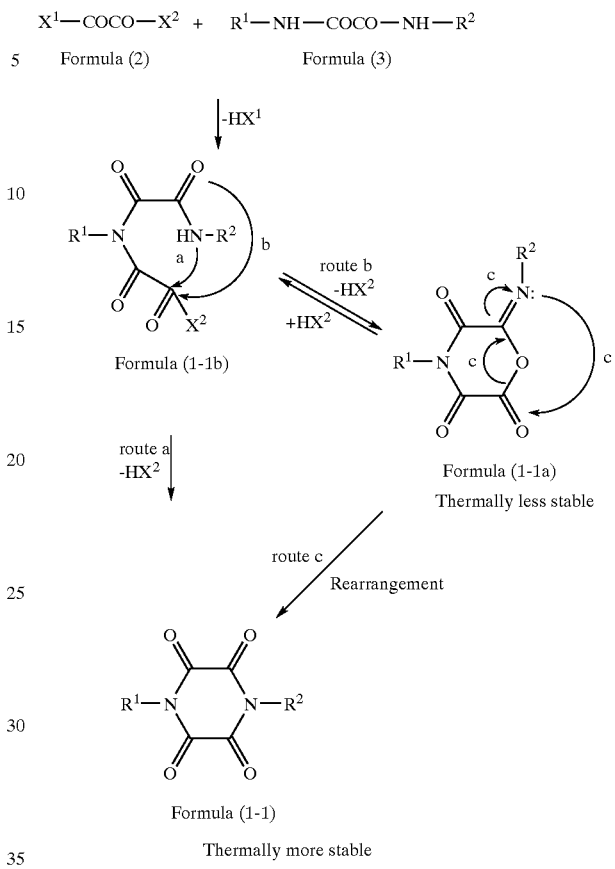

Scheme 4

Preferably, the water or the aqueous alkali solution is added to the reaction mixture after the evolution of hydrogen halide is greater than 40% complete, more preferably 60% complete, and furthermore preferably 80% complete. The hydrogen 5 halide is a reaction product of the oxalyl halide and the oxamide reaction (see Scheme 4). Note that between using water and the aqueous alkali solution, water is preferred due to its low cost/safety.

In general, the resultant mono(tetraketopiperazine) compound is obtained from solution as precipitates. In order to obtain a high yield of the product, it is preferable that the reaction mixture is cooled to between −20° C. and 40° C., and preferably from −10° C. to 30° C. The resultant precipitate is filtered using any number of well known methods within the art. Preferably, the precipitate is filtered using a glass filter, paper filter, cloth filter, or the like. The precipitate may then be washed with water and solvent, for example acetonitrile, ether, and acetone. When the resultant mono (tetraketopiperazine) compound does not appear as precipitates, other well known methods within the art may be applied to the isolation of the product; for example, concentration or a evaporation of the solvent of the reaction mixture, followed by the crystallization of the product.

In order to confirm the identity of the product, decomposition point, NMR spectrum, IR spectrum and Mass spectrum may be performed, and compared to the known corresponding values for the mono(tetraketopiperazine) compound in the art. Other known tests or analyses may also be performed to determine the yield and percent purity of the mono(tetraketopiperazine) compound.

Using the above embodiments, it is believed that from about 60 to 90% yield may be expected, and in some cases may be as high as from 70 to 90%.

Method B: The Reaction of Oxalyl Halide and Silylamine

Another embodiment of the present invention relates to a process for preparing the mono(tetraketopiperazine) compound represented by formula (1-1) wherein $R^1$ and $R^2$ are the same ($R^1=R^2$), by reacting an oxalyl halide represented by formula (2) and a silylamine represented by formula (4) (see Scheme 5).

Scheme 5 (Method B)

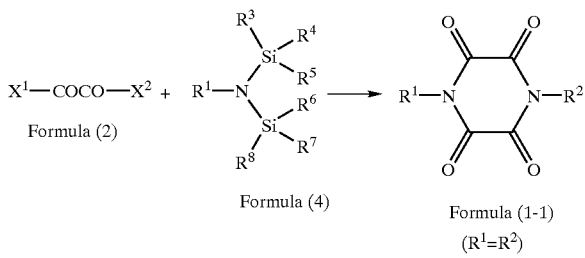

Formula (2)    Formula (4)    Formula (1-1)
                              ($R^1=R^2$)

Compounds

The term oxalyl halide is the same as described in Method A.

The term silylamine refers to any compound having a chemical formula (4), where $R^1$ is defined above and $R^3$, $R^4$, $R^5$, $R^6$, $R^7$, and $R^8$ are independently a substituted or unsubstituted alkyl or aryl group. $R^3$–$R^8$ are preferably an alkyl group consisting of 1 to 10 carbon atoms which is unsubstituted or substituted with one or more substituents selected from the group consisting of a halogen atom and an aryl group, or an aryl group consisting of 6 to 10 carbon atoms which is unsubstituted or substituted with one or more substituents selected from the group consisting of a halogen atom and an alkyl group. Preferable alkyl groups for $R^3$–$R^8$ include methyl, ethyl, propyl, isopropyl, butyl, isobutyl, tert-butyl, and benzyl, and preferable aryl groups for $R^3$–$R^8$ include phenyl, o-, m-, or p-tolyl, and xylyl. $R^3$–$R^8$ are more preferably an alkyl group consisting of 1 to 4 carbon atoms which is unsubstituted or substituted with one or more substituents selected from the group shown above, or an aryl group consisting of 6 to 8 carbon atoms which is unsubstituted or substituted with one or more substituents selected from the group shown above.

The silylamines are commercially available or easy to prepare according to technology well known in the art. Preferable silylamines for use in the present invention include: bis(trimethylsilyl)amine (hexamethyldisilazane), bis(dimethylethylsilyl)amine, bis(dimethylphenyl)amine, bis(triethylsilyl)amine, bis(tripropylsilyl)amine, bis(tributylsilyl)amine, N,N-bis(trimethylsilyl)methylamine (heptamethyldisilazane), N,N-bis(trimethylsilyl)ethylamine, N,N-bis(trimethylsilyl)propylamine, N,N -bis(trimethylsilyl)isopropylamine, N,N-bis(trimethylsilyl)butylamine, N,N-bis(trimethylsilyl)pentylamine, N,N-bis(trimethylsilyl)cyclopentylamine, N,N-bis(trimethylsilyl)hexylamine, N,N-bis(trimethylsilyl)cyclohexylamine, N,N-bis(trimethylsilyl)heptylamine, N,N-bis(trimethylsilyl)octylamine, N,N-bis(trimethylsilyl)nonylamine, N,N-bis(trimethylsilyl)decylamine, N,N -bis(trimethylsilyl)aniline, o-, m-, or p-[N,N-bis(trimethylsilyl)methyl]aniline, N,N -bis(trimethylsilyl)dimethylaniline, and N,N-bis(trimethylsilyl)naphthylamine.

Solvent is not necessary for the reaction. However, it is preferable to use a solvent in order to make the reaction smooth and safe and to obtain a high yield of the product. Examples of suitable solvents for use with the present invention include halocarbons such as dichloromethane, chloroform, carbon tetrachloride, dichloroethane, trichloroethane, tetrachloroethane; nitriles such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ether, diisobutyl ether, and dibutyl ether; esters such as ethyl acetate, methyl acetate, and methyl propionate; hydrocarbons such as pentane, hexane, heptane, octane, nonane, and decane; and mixtures thereof. The most preferred solvents for use with the present invention are halocarbons and nitriles.

The Process

An embodiment of the invention for producing the mono (tetraketopiperazine) compound represented by formula (1-1) wherein $R^1=R^2$ is a process that comprises: reacting an oxalyl halide represented by formula (2) and a silylamine represented by formula (4) while using a molar ratio of from 1:10 to 10:1, respectively, and preferably from 1:5 to 5:1, and more preferably from 2:1 to 1:2, and furthermore preferably from 1.5:1 to 1:1.5. The reactants are mixed at between –50° C. and 200° C., and preferably between –20° C. and 150° C., and most preferably between 10° C. and 100° C. Since the reaction time depends on the reaction conditions (temperature, molar ratio, solvent, and others), the reaction time may vary for each reaction.

In general, the resultant mono(tetraketopiperazine) compound is obtained from the reaction mixture in a similar manner as described in Method A above. Confirming the identity of the product is described in Method A.

Method C: The Reaction of Oximidyl Halide and Amine

Another embodiment of the present invention relates to a process for preparing a mono(tetraketopiperazine) compound represented by formula (1-1) by reacting an oximidyl halide represented by formula (5) and an amine represented by formula (6) (see Scheme 6).

Scheme 6 (Method C)

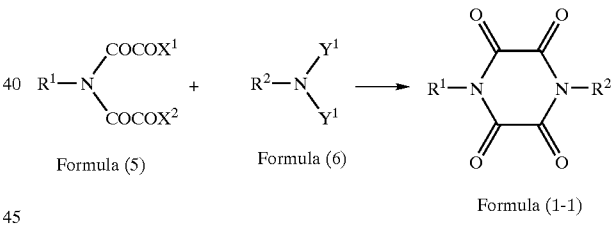

Formula (5)    Formula (6)

Formula (1-1)

Compounds

The term oximidyl halide refers to any compound having a chemical formula as represented by formula (5), where $R^1$, $X^1$, and $X^2$ are defined above. The oximidyl halide can be easily and effectively prepared by the process of this invention described below. The oximidyl halides employed in the present invention preferably include: $HN(COCOF)_2$, $HN(COCOCl)_2$, $HN(COCOBr)_2$, $HN(COCOI)_2$, $CH_3N(COCOF)_2$, $CH_3N(COCOCl)_2$. $C_2H_5N(COCOCl)_2$, $C_3H_7N(COCOCl)_2$, iso-$C_3H_7N(COCOCl)_2$, cyclo-$C_3H_7N(COCOCl)_2$, $C_4H_9N(COCOCl)_2$, iso-$C_4H_9N(COCOCl)_2$, tert-$C_4H_9N(COCOCl)_2$, $C_5H_{11}N(COCOCl)_2$, cyclo-$C_5H_9N(COCOCl)_2$, $C_6H_{13}N(COCOCl)_2$, cyclo-$C_6H_{11}N(COCOCl)_2$, $C_7H_{15}N(COCOCl)_2$, $C_8H_{17}N(COCOBr)_2$, $C_9H_{19}N(COCOI)_2$, $C_{10}H_{21}N(COCOF)_2$, $C_6H_5N(COCOCl)_2$, $CH_3C_6H_4N(COCOCl)_2$, $ClC_6H_4N(COCOCl)_2$, $FC_6H_4N(COCOCl)_2$, $CH_3OC_6H_4N(COCOCl)_2$, and $O_2NC_6H_4N(COCOCl)_2$, $C_{10}H_7N(COCOCl)_2$ (iso-$C_3H_7$ is an isopropyl group; cyclo-$C_3H_7$, cyclopropyl; iso-$C_4H_9$, isobutyl; tert-$C_4H_9$, tert-butyl; $C_5H_{11}$, pentyl; $C_6H_{13}$, hexyl; $C_7H_{15}$, heptyl; $C_8H_{17}$, octyl; $C_9H_{19}$, nonyl; $C_{10}H_{21}$, decyl; $C_6H_5$, phenyl; $C_6H_4$, o-, m-, or p-phenylene; and $C_{10}H_7$, 1- or 2-naphtyl group).

The amine refers to any compound of the chemical formula as represented by formula (6), where $R^2$ is the same as described above, and $Y^1$ and $Y^2$ are independently a hydrogen atom, $SiR^3R^4R^5$, or $SiR^6R^7R^8$, wherein $R^3$, $R^4$, $R^5$, $R^6$, $R^7$, and $R^8$ are the same as described above. The amines are commercially available or easy to prepare according to technology well known in the art. The amines employed in the present invention preferably include; amine, methylamine, ethylamine, propylamine, isopropylamine, cyclopropylamine, butylamine, isobutylamine, tert-butylamine, pentylamine, cyclopentylamine, hexylamine, cyclohexylamine, heptylamine, octylamine, nonylamine, decylamine, aniline, o-, m-, or p-methylaniline, fluoroaniline, chloroaniline, bromoaniline, iodoaniline, nitroaniline, acetylaniline, methoxyaniline, (acetylamino)aniline, (methylthio)aniline, (methanesulfonyl)aniline, dimethylaniline, 1 or 2-naphtylamine, (trimethylsilyl)amine, bis(trimethylsilyl) amine (hexamethyldisilazane), (dimethylethylsilyl)amine, (dimethylphenylsilyl)amine, (methyldiphenylsilyl)amine, (triphenylsilyl)amine, bis(dimethylethylsilyl)amine, bis (triethylsilyl)amine, bis(tripropylsilyl)amine, bis (tributylsilyl)amine, N-(trimethylsilyl)methylamine, N,N-bis(trimethylsilyl)methylamine (heptamethyldisilazane), N-(trimethylsilyl)ethylamine, N,N-bis(trimethylsilyl) ethylamine, N,N-bis(trimethylsilyl)propylamine, N,N-bis (trimethylsilyl)butylamine, N,N-bis(trimethylsilyl) pentylamine, N,N-bis(trimethylsilyl)hexylamine, N,N-bis (trimethylsilyl)heptylamine, N,N-bis(trimethylsilyl) octylamine, N,N-bis(trimethylsilyl)nonylamine, N,N-bis (trimethylsilyl)decylamine, N-(trimethylsilyl)aniline, N,N-bis(trimethylsilyl)aniline, N -(trimethylsilyl)- o-, m-, or p-methylaniline, N-(trimethylsilyl)-fluoroaniline, N-(trimethylsilyl)-chloroaniline, N-(trimethylsilyl)-bromoaniline, N-(trimethylsilyl)-iodoaniline, N-(trimethylsilyl)-nitroaniline, N-(trimethylsilyl)-methoxyaniline, N-(trimethylsilyl)-(methylthio)aniline, and 1- or 2-N-(trimethylsilyl)naphthylamine.

Solvent is not necessary for the reaction. However, it is preferable to use a solvent in order to make the reaction smooth and safe and to obtain a high yield of the product. Examples of suitable solvents for use with the present invention include halocarbons such as dichloromethane, chloroform, carbon tetrachloride, dichloroethane, trichloroethane, tetrachloroethane; nitriles such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ethers, diisobutyl ether, and dibutyl ether; esters such as ethyl acetate, methyl acetate, and methyl propionate; hydrocarbons such as pentane, hexane, heptane, octane, nonane, and decane; and these mixtures. The most preferred solvents for use with the present invention are halocarbons and nitrites.

The Process

An embodiment of the invention for producing the mono (tetraketopiperazine) compound represented by formula (1-1) is a process that comprises: reacting an oximidyl halide represented by formula (5) and an amine represented by formula (6) using a molar ratio of from 1:10 to 10:1, respectively, and is preferably from 1:2 to 2:1, and more preferably from 1:1.5 to 1.5:1. The reactants are mixed at between −50° C. and 200° C., and preferably between −20° C. and 150° C., and most preferably between 10° C. and 100° C. Since the reaction time depends on the reaction conditions (temperature, molar ratio, solvent, and others), the reaction time may be chosen for each reaction.

In general, the resultant mono(tetraketopiperazine) compound is obtained from the reaction mixture in a similar manner as described in Method A above. Confirming the identity of the product is described in Method A.

Method D: The Reaction of Oxalyl Halide and Silylamine, and the Reaction with an Amine Another embodiment of the present invention relates to a process for preparing the mono(tetraketopiperazine) compound represented by formula (1-1) by reacting an oxalyl halide represented by formula (2) and a silylamine represented by formula (4), and reacting with an amine represented by formula (6) (see Scheme 7).

Scheme 7 (Method D)

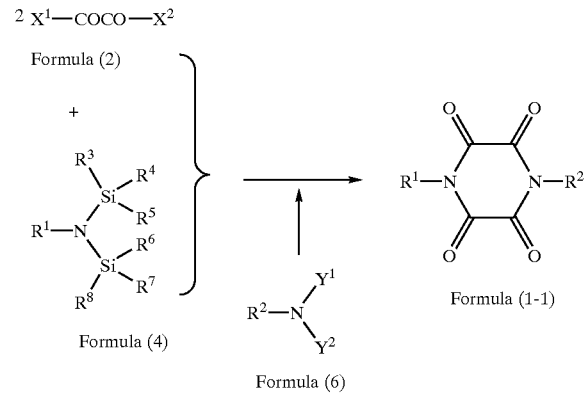

Compounds

The term oxalyl halide is the same as in Method A. The oxaly halide employed for the present invention is shown in Method A. The term silylamine is the same as in Method B. The silylamine employed for the present invention is shown in Method B. The term amine is the same as in Method C. The amine employed for the present invention is shown in Method C.

Solvent is not necessary for the reaction. However, it is preferable to use a solvent in order to make the reaction smooth and safe and to obtain a high effectiveness and yield of the product. Examples of suitable solvents for use with the present invention include halocarbons such as dichloromethane, chloroform, carbon tetrachloride, dichloroethane, trichloroethane, tetrachloroethane; nitrites such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ether, diisobutyl ether, and dibutyl ether; esters such as ethyl acetate, methyl acetate, and methyl propionate; hydrocarbons such as pentane, hexane, heptane, octane, nonane, and decane; and these mixtures. The most preferred solvents for use with the present invention are halocarbons and nitrites due to high yields.

The Process

An embodiment of the invention for producing the mono(tetraketopiperazine) compound represented by formula (1-1) is a process that comprises: (Step 1) reacting an oxalyl halide represented by formula (2) and a silylamine represented by formula (4), and (Step 2) reacting with an amine represented by formula (6).

Step 1

The reactants are mixed in the presence or absence of a solvent at between −80° C. and 100° C., and preferably between −50° C. and +50° C., and most preferably between −30° C. and +30° C. Without a solvent, it is preferable to use a large excess of the oxalyl halide; the molar ratio of 20:1 to 5:1 of the oxalyl halide: the silylamine, and more preferably 15:1 to 5:1. With a solvent, it is preferable to use the molar ratio of 5:1 to 1.5:1, and more preferably 3:1 to 1.8:1. In general, it is preferable to use the solvent in order to obtain a high effectiveness of production. Since the reaction time depends on the reaction conditions (temperature, molar ratio, solvent, and others), the reaction time may be chosen for each reaction. The reaction mixture may be used for Step 2 without further treatment, or the excess of the oxalyl halide, byproducts, and/or solvent having low boiling points may be evaporated up from the reaction mixture so that a substance having a high boiling point leaves. The substance comprises an oximidyl halide represented by formula (5) and can be used for the next Step 2. From a viewpoint of the yield and purity of the final product, the mono(tetraketopiperazine) represented by formula (1-1), it is preferable to use the substance having a high boiling point rather than the reaction mixture of the Step 1.

Step 2

The reaction of Step 2 may be carried out in the presence or absence of a solvent, but it is preferable to use the solvent in order to obtain a high yield and purity of the mono(tetraketopiperazine) compound. The amine is added to the reaction mixture obtained in Step 1 or to the substance having a high boiling point, obtained in Step 1, or a solution of the substance in an appropriate solvent. The solvents are exemplified above. The amount of the amine used is from 0.5:1 to 5:1 molar ratio of the amine: the silylamine used in Step 1, preferably from 0.7:1 to 2:1, and more preferably from 0.8:1 to 1.5:1. The reaction temperature is between −50° C. and +200° C., preferable −20° C. and +150° C., more preferable 10° C. and 100° C. Since the reaction time depends on the reaction conditions (temperature, molar ratio, solvent, and others), the reaction time may vary for each reaction.

In general, the resultant mono(tetraketopiperazine) compound is obtained from the reaction mixture in a similar manner as described in Method A above. Confirming the identity of the product is described in Method A.

Process for Preparing Di(tetraketopiperazine) Compound Represented by Formula (1-2)

Method E: The Reaction of Oxalyl Halide and Dioxamide

Another embodiment of the present invention relates to a process for preparing the di(tetraketopiperazine) compound represented by formula (1-2) by reacting an oxalyl halide represented by formula (2) and a dioxamide represented by formula (7), and, preferably, adding water or an aqueous alkali solution to the reaction mixture (see scheme 8).

Scheme 8 (Method E)

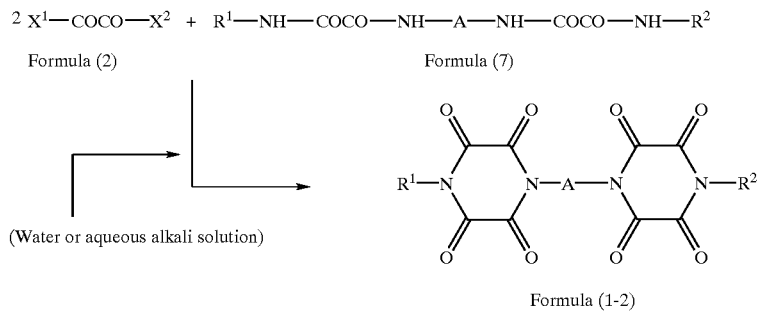

Formula (1-2)

Compounds

The term oxalyl halide is the same as described in Method A. The term dioxamide refers to any compound having a chemical formula (7), where $R^1$, $R^2$, and A are defined above. The dioxamides are easy to prepare according to known methods as follows: Oxamides in which $R^1=R^2$ may be prepared by the reaction of diamine represented by formula (8) shown later and ethyl chlorooxoacetate, followed by the treatment with an amine represented by formula (6). The oxamides, in which $R^1$ and $R^2$ are not the same, can be prepared by the reaction of diamine represented by formula (8) and ethyl chlorooxoacetate, followed by treatment with a kind of amine represented by formula (6) and then with another kind of amine represented by formula (6).

The dioxamides employed in the present invention preferably include: $H_2N$—COCO—NH—$CH_2CH_2$—NH—$COCONH_2$, $CH_3NH$—COCO—NH—$(CH_2)_2$—NH—COCO—$NHCH_3$, $CH_3NH$—COCO—NH—$(CH_2)_3$—NH—COCO—$NHCH_3$, $CH_3NH$—COCO—NH—CH$(CH_3)CH_2$—$NHCH_3$, $CH_3NH$—COCO—NH—$(CH_2)_4$—NH—COCO—$NHCH_3$, $CH_3NH$—COCO—NH—$(CH_2)_5$—NH—COCO—$NHCH_3$, $CH_3NH$—COCO—NH—$(CH_2)_6$—NH—COCO—$NHCH_3$, $CH_3NH$—COCO—NH—$(CH_2)_7$—NH—COCO—$NHCH_3$, $CH_3NH$—COCO—NH—$(CH_2)_8$—NH—COCO—$NHCH_3$, $CH_3NH$—COCO—NH—$(CH_2)_9$—NH—COCO—$NHCH_3$, $CH_3NH$—COCO—NH—$(CH_2)_{10}$—NH—COCO—$NHCH_3$, $CH_3CH_2NH$—COCO—NH—$(CH_2)_2$—NH—COCO—$NHCH_2CH_3$, $CH_3(CH_2)_2NH$—COCO—NH—$(CH_2)_2$—NH—COCO—$NH(CH_2)_2CH_3$, $CH_3(CH_2)_3NH$—COCO—NH—$(CH_2)_2$—NH—COCO—$NH(CH_2)_3CH_3$, $C_6H_5NH$—COCO—NH—$(CH_2)_2$—NH—COCO—$NHC_6H_5$, $CH_3C_6H_4NH$—COCO—NH—$(CH_2)_2$—NH—COCO—NH—$C_6H_4CH_3$, $FC_6H_4NH$—COCO—NH—$(CH_2)_2$—NH—COCO—$NHC_6H_4F$, $CH_3NH$—COCO—NH-o-$C_6H_4$—NH—COCO—$NHCH_3$, $CH_3NH$—COCO—NH-m-$C_6H_4$—NH—COCO—$NHCH_3$, $CH_3NH$—COCO—NH-p-$C_6H_4$—NH—COCO—$NHCH_3$, $CH_3NH$—COCO—NH-o, m, or p-$(CH_3C_6H_3)$—NH—COCO—$NHCH_3$, $CH_3NH$—COCO—NH— o, m, or p-$[(CH_3)(CH_3)$ $C_6H_2$]—NH—COCO—NHCH$_3$, CH$_3$NH—COCO—NH—o, m, or p-(FC$_6$H$_3$)—NH—COCO—NHCH$_3$, CH$_3$NH—COCO—NH— o, m, or p-(ClC$_6$H$_3$)—NH—COCO—NHCH$_3$, CH$_3$NH—COCO—NH— o, m, or p-C$_6$F$_4$—NH—COCO—NHCH$_3$, CH$_3$NH—COCO—NH— o, m, or p-(CNC$_6$H$_3$)—NH—C OCO—NHCH$_3$, CH$_3$NH—COCO—NH— o, m, or p-(NO$_2$C$_6$H$_3$)—NH—COCO—NHCH$_3$, C$_2$H$_5$NH—COCO—NH— o, m, or p-C$_6$H$_4$—NH—COCO—NHC$_2$H$_5$, C$_2$H$_5$NH—COCO—NH— o, m, or p-C$_6$F$_4$—NH—COCO—NHC$_2$H$_5$, C$_3$H$_{7NH—COCO—NH—\ o,\ m,\ or\ p-}$C$_6$H$_4$—NH—COCO—NHC$_3$H$_7$, C$_4$H$_9$NH—COCO—NH— o, m, or p-C$_6$H$_{4—NH—\ COCO—NHC}$$_4$H$_9$, and C$_6$H$_5$NH—COCO—NH— o, m, or p-C$_6$H$_4$—NH—COCO—NHC$_6$H$_5$ [C$_6$H$_5$ is a phenyl group, -o—C$_6$H$_4$— means ortho-phenylene group, -m-C$_6$H$_4$— means meta-phenylene group, -p-C$_6$H$_4$— means para-phenylene group, -p-(CH$_3$C$_6$H$_3$) — means para-methylphenylene group, -p-[(CH$_3$)(CH$_3$)C$_6$H$_2$]— means para-dimethylphenylene group, -p-(FC$_6$H$_3$) — means para-fluorophenylene group, and -p-(ClC$_6$H$_3$)— means para-chlorophenylene group, -o-C$_6$F$_4$— means ortho-tetrafluorophenylene group, -m-C$_6$F$_4$— means meta-tetrafluorophenylene group, and -p-C$_6$F$_4$— means para-tetrafluorophenylene group, -p-(CNC$_6$H$_3$) — means para-cyanophenylene group, and -p-(NO$_2$C$_6$H$_3$) — means para-nitrophenylene group].

Solvent is not necessary for the reaction. However, it is preferable to use a solvent in order to make the reaction smooth and safe and to obtain a high effectiveness and yield of the product. Examples of suitable solvents for use with the present invention include halocarbons such as dichloromethane, chloroform, carbon tetrachloride, dichloroethane, trichloroethane, tetrachloroethane; nitriles such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ether, diisobutyl ether, and dibutyl ether; esters such as ethyl acetate, methyl acetate, and methyl propionate; hydrocarbons such as pentane, hexane, heptane, octane, nonane, and decane; and these mixtures. The most preferred solvents for use with the present invention are nitriles such as acetonitrile due to better yields.

The term alkali of the aqueous alkali solution is the same as defined in Method A above. The amount of the water or the aqueous alkali solution is the same as described in Method A.

Use of an aqueous acid solution other than water or an aqueous alkali solution is included in the use of water in this invention, because a large amount of a hydrogen halide that has a strong acidic nature is formed by the reaction of the dioxamide and the oxalyl halide in a similar manner as in Method A, and thus the added water becomes an aqueous acid solution.

The Process

An embodiment of the invention for producing di(tetraketopiperazine) compound represented by formula (1-2) is a process that comprises: reacting an oxalyl halide represented by formula (2) and a dioxamide represented by formula (7) with using a molar ratio of from 1:1 to 1000:1, respectively, and is preferably from 1.5:1 to 100:1, more preferably from 1.8:1 to 50:1. The reactants are mixed at between −50° C. and 200° C., and preferably between −20° C. and 150° C., and most preferably between 10° C. and 100° C. The reaction is allowed to stir and, preferably, to add water or an aqueous alkali solution to the reaction mixture. Since the reaction time depends on the reaction conditions (temperature, molar ratio, solvent, and others), the reaction time may vary for each reaction.

It is not necessary to add water or an aqueous alkali solution to the reaction mixture, but it is preferable in order to obtain the better yield of the product. The time when the water or the aqueous alkali solution is added to the reaction mixture is the same as described in Method A.

In general, the resultant tetraketopiperazine compound is obtained from the reaction mixture in a similar manner as described in Method A above. Confirming the identity of the product is described in Method A.

Method F: The Reaction of Oximidyl Halide and Diamine

Another embodiment of the present invention relates to a process for preparing a di(tetraketopiperazine) compound represented by formula (1-2) wherein $R^1=R^2$ by reacting an oximidyl halide represented by formula (5) and a diamine represented by formula (8) (see Scheme 9).

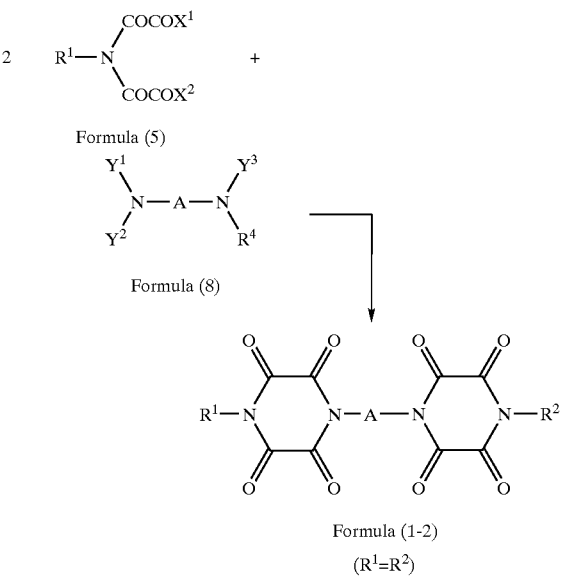

Scheme 9 (Method F)

Formula (5)

Formula (8)

Formula (1-2)

($R^1=R^2$)

Compounds

The term oximidyl halide is the same as described in Method C. The term diamine refers to any compound having the chemical formula as represented by formula (8), where A is defined above, and $Y^1$, $Y^2$, $Y^3$, and $Y^4$ are independently a hydrogen atom, $SiR^3R^4R^5$, $SiR^6R^7R^8$, $SiR^9R^{10}R^{11}$, or $SiR^{12}R^{13}R^{14}$. $R^3$, $R^4$, $R^6$, $R^7$, $R^8$, $R^9$, $R^{10}$, $R^{11}$, $R^{12}$, $R^{13}$, and $R^{14}$ are independently a substituted or unsubstituted alkyl or aryl group. $R^3$–$R^{14}$ are preferably an alkyl group consisting of 1 to 10 carbon atoms which is unsubstituted or substituted with one or more substituents selected from the group consisting of a halogen atom and an aryl group, or an aryl group consisting of 6 to 10 carbon atoms which is unsubstituted or substituted with one or more substituents selected from the group consisting of a halogen atom and an alkyl group. Preferable substituted or unsubstituted alkyl groups for $R^3$–$R^{14}$ include methyl, ethyl, propyl, isopropyl, butyl, isobutyl, t-butyl, and benzyl, and preferable substituted or unsubstituted aryl groups for $R^3$–$R^{14}$ include phenyl, o-, m-, or p-tolyl, and xylyl. $R^3$–$R^{14}$ are more preferably an alkyl group consisting of 1 to 4 carbon atoms which is unsubstituted or substituted with one or more substituents selected from the group shown above, or an aryl group consisting of 6 to 8 carbon atoms which is unsubstituted or substituted with one or more substituents selected from the group shown above.

The diamines are commercially available or easy to prepare according to technology well known in the art.

Preferably, diamines employed in the present invention include: $H_2N-(CH_2)_2-NH_2$, $(H_3C)_3SiHN-(CH_2)_2-NHSi(CH_3)_2$, $[(H_3C)_3Si]_2N-(CH_2)_2-NHSi(CH_3)_3$, $[(H_3C)_3Si]_2N-(CH_2)_2-N[Si(CH_3)_2]_2$, $H_2N-(CH_2)_3-NH_2$, $(H_3C)_3SiHN-(CH_2)_3-NHSi(CH_3)_3$, $H_2N-CH(CH_3)CH_2-NH_2$, $(H_3C)_3SiHN-CH(CH_3)CH_2-NHSi(CH_3)_3$, $H_2N-(CH_2)_4-NH_2$, $(H_3C)_3SiHN-(CH_2)_4-NHSi(CH_3)_3$, $H_2N-(CH_2)_5-NH_2$, $H_2N-(CH_2)_6-NH_2$, $H_2N-(CH_2)_8-NH_2$, $H_2N-(CH_2)_{10}-NH_2$, $H_2N$-o, m, or p-$C_6H_4-NH_2$, $(CH_3)_3SiNH$- o, m, or p-$C_6H_4$-NHSi$(CH_3)_3$, $H_2H$- o, m, or p-$(CH_3C_6H_3)-NH_2$, $H_2H$- o, m, or p-$[(CH_3)(CH_3)C_6H_2]-NH_2$, $H_2H$- o, m, or p-$(FC_6H_3)-NH_2$, $H_2H$- o, m, or p-$(ClC_6H_3)-NH_2$, $H_2H$- o, m, or p-$C_6F_4-NH_2$, $H_2H$- o, m, or p-$C_6Cl_4$-NH_2 (the definitions of -o-$C_6H_4$- etc. are shown above).

Solvent is not necessary for the reaction. However, it is preferable to use a solvent in order to make the reaction reproducible and safe and to obtain a high yield of the product. Examples of suitable solvents for use with the present invention include halocarbons such as dichloromethane, chloroform, carbon tetrachloride, dichloroethane, trichloroethane, tetrachloroethane; nitriles such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ether, diisobutyl ether, and dibutyl ether; hydrocarbons such as pentane, hexane, heptane, octane, nonane, and decane; and these mixtures. Preferred solvents for use with the present invention are halocarbons and nitriles, more preferred solvents are nitriles, and the most preferred solvent is acetonitrile due to high yields.

The Process

An embodiment of the invention for producing di(tetraketopiperazine) compounds represented by formula (1-2) is a process that comprises: reacting an oximidyl halide represented by formula (5) and a diamine represented by formula (8) using a molar ratio of from 1:1 to 10:1, respectively, and is preferably from 1.5:1 to 5:1, and more preferably from 1.8:1 to 2.5:1. The reactants are mixed at between −50° C. and 200° C., and preferably between −20° C. and 150° C., and most preferably between 10° C. and 100° C. Since the reaction time depends on the reaction conditions (temperature, molar ratio, solvent, and others), the reaction time may vary for each reaction.

In general, the resultant di(tetraketopiperazine) compound is obtained from the reaction mixture in a similar manner as described in Method A above. Confirming the identity of the product is described in Method A.

Method G: The Reaction of Oxalyl Halide and Silylamine, and the Reaction with Diamine Another embodiment of the present invention relates to a process for preparing the di(tetraketopiperazine) compound represented by formula (1-2) wherein $R^1=R^2$ by reacting an oxalyl halide represented by formula (2) and a silylamine represented by formula (4), and reacting with a diamine represented by formula (8) (see Scheme 10).

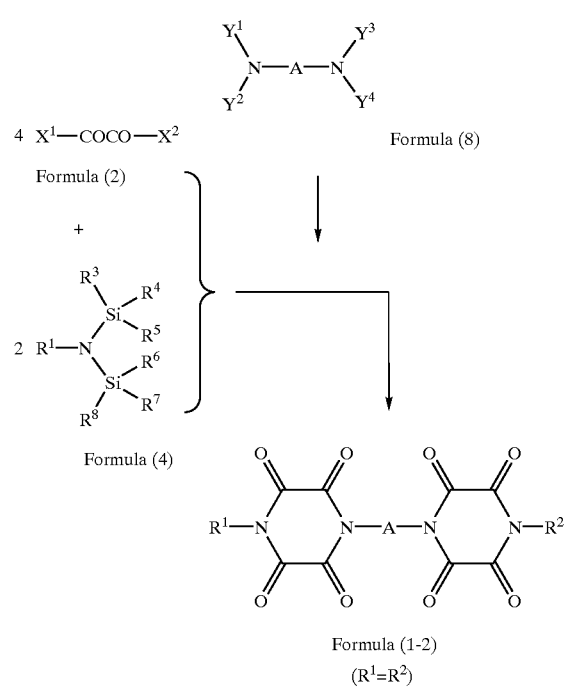

Scheme 10 (Method G)

Compounds

The term oxalyl halide is the same as described in Method A. The oxaly halide employed for the present invention is shown in Method A. The term silylamine is the same as described in Method B. The silylamine employed for the present invention is shown in Method B. The term diamine is the same as described in Method F. The diamine employed for the present invention is shown in Method F.

Solvent is not necessary for the reaction. However, it is preferable to use a solvent in order to make the reaction smooth and safe and to obtain a high yield of the product. Examples of suitable solvents for use with the present invention include halocarbons such as dichloromethane, chloroform, carbon tetrachloride, dichloroethane, trichloroethane, tetrachloroethane; nitriles such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ether, diisobutyl ether, and dibutyl ether; esters such as ethyl acetate, methyl acetate, methyl propionate, and ethyl propionate; hydrocarbons such as pentane, hexane, heptane, octane, nonane, and decane; and these mixtures. The most preferred solvents for use with the present invention are halocarbons and nitrites due to high yields.

The Process

An embodiment of the invention for producing the di(tetraketopiperazine) compound represented by formula (1-2) is a process that comprises: (Step 1) reacting an oxalyl halide represented by formula (2) and a silylamine represented by formula (4), and (Step 2) reacting with a diamine represented by formula (8).

Step 1

The step is the same as described in Step 1 in Method D above.

Step 2

The reaction of Step 2 may be carried out in a solvent or without a solvent, but it is preferable to use the solvent in order to obtain a high yield and purity of the di(tetraketopiperazine) compound. The diamine is added to the reaction mixture obtained in Step 1 or to the substance having a high boiling point, obtained in Step 1, or a solution of the substance in an appropriate solvent. The solvents are exemplified above. The amount of the diamine used is from 1:1 to 1:10 molar ratio of the diamine:the silylamine used in Step 1, preferably from 1:1.5 to 1:5, and more preferably from 1:1.7 to 1:3. The reaction temperature is between −50° C. and +200° C., preferable −20° C. and +150° C., more preferable 10° C. and 100° C. Since the reaction time depends on the reaction conditions (temperature, molar ratio, solvent, and others), the reaction time may vary for each reaction.

In general, the resultant di(tetraketopiperazine) compound is obtained from the reaction mixture in a similar manner as described in Method A above. Confirming the identity of the product is described in Method A.

Process for Preparing Oximidyl Halide Represented by Formula (5)

N-Ethyl oximidyl chloride [formula (5); $R^1=C_2H_5$, $X^1=X^2=Cl$] was prepared from the reaction of oxalyl chloride and ethylamine hydrochloride, but the method for the preparation was not satisfactory from a viewpoint of ineffectiveness of the process, in which a very large amount of oxalyl chloride was used and the reaction time was very long (50 hours) [R. N. McDonald, *Journal of Organic Chemistry*, Vol. 24, p 1580 (1959)]. The present invention has been developed against this drawback.

One embodiment of the present invention relates to a process for preparing an oximidyl halide represented by formula (5) by reacting an oxalyl halide represented by formula (2) and a silylamine represented by formula (4) (see Scheme 11).

Scheme 11

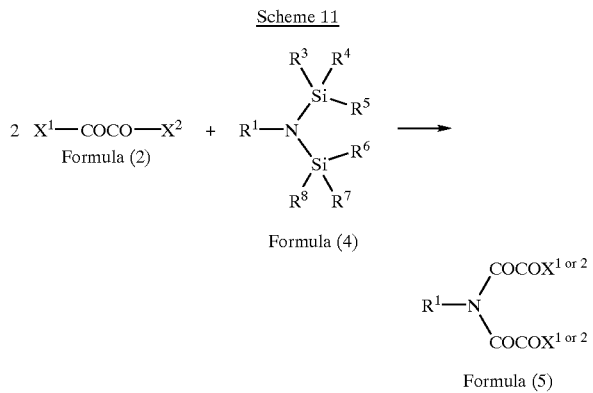

Compounds

The term oxalyl halide is the same as described in Method A. The term silylamine is the same as described in Method B. Solvent is not necessary for the reaction. However, it is preferable to use a solvent in order to make the reaction smooth and safe and to obtain a high yield of the product. Examples of suitable solvents for use with the present invention include halocarbons such as dichloromethane, chloroform, carbon tetrachloride, dichloroethane, trichloroethane, tetrachloroethane; nitriles such as acetonitrile, propionitrile, and benzonitrile; aromatics such as benzene, chlorobenzene, dichlorobenzene, fluorobenzene, toluene, xylene, and benzotrifluoride; ethers such as diethyl ether, dipropyl ether, diisobutyl ether, and dibutyl ether esters such as ethyl acetate, methyl acetate, methyl propionate, and ethyl propionate; hydrocarbons such as pentane, hexane, heptane, octane, nonane, and decane; and these mixtures. The most preferred solvents for use with the present invention are halocarbones such as dichloromethane, chloroform, and dichloroethane, and nitrites such as acetonitrile due to high yields.

The Process

An embodiment of the invention for producing the oximidyl halide represented by formula (5) is a process that comprises: reacting an oxalyl halide represented by formula (2) and a silylamine represented by formula (4). The reactants are mixed in a solvent or without a solvent at between −80° C. and 100° C., and preferably between −50° C. and +50° C., and most preferably between −30° C. and +30° C. Without a solvent, it is preferable to use a large excess of the oxalyl halide; the molar ratio of 100:1 to 5:1 of the oxalyl halide:the silylamine, and more preferably 50:1 to 5:1. With a solvent, it is preferable to use the molar ratio of 5:1 to 1.5:1, and more preferably 3:1 to 1.8:1. In general, it is preferable to use the solvent in order to obtain a high effectiveness of production. The reaction time is less than 24 hours, and the reaction time may be chosen for the reaction each as the reaction time depends on the reaction conditions (temperature, molar ratio, solvent, and others).

After the reaction, the solvent, the excess of the oxalyl halide, and/or byproducts having low boiling points are evaporated up to leave an almost pure product of formula (5), which can be used as a starting material for the process of Methods C or F described above. If necessary, usual methods such as distillation under reduced pressure and/or recrystallization from an appropriate solvent may be applied to the purification of the product.

Another embodiment of the present invention are new compounds, N,N'-diethyl-2,3,5,6-tetraketopiperazine [formula(1-1) wherein $R^1=R^2=C_2H_5$] and N-alkyl-N'-aryl-2,3,5,6-tetraketopiperazine [formula (1-1) wherein $R^1$=alkyl, $R^2$=aryl] wherein the alkyl and the aryl are defined as above, and the di(tetraketopiperazine) compounds of the formula (1-2), which are useful in the present invention of the application to the battery materials. N,N'-Diethyl-2,3,5,6-tetraketopiperazine is definitely different from the related compound, N,N'-dimethyl-2,3,5,6-tetraketopiperazine, which was only an identified compound [see; M. J Th. Bornwater, *Rec. D. Trav. Chim.*, Vol. 31, p.p. 129–131 (1912)] in the series of N,N'-dialkyl-2,3,5,6-tetraketopiperazine, has no melting point and decomposes at about 380° C. Because N,N'-diethyl-2,3,5,6-tetraketopiperazine melts at 253–255° C. without decomposition, it is possible to make it into a thin layered film or to paint it on an electrode plate by heating. In a literature [R. N. McDonald, *Journal of Organic Chemistry*, Vol. 24, p.p. 1580–1581 (1959)], he described that a trace amount of crystals obtained as a byproduct by his reaction was believed to be N,N'-diethyltetraketopiperazine, but he obtained no analytical data.

Having generally described the invention, the same will be more readily understood by reference to the following examples, which are provided by way of illustration and are not intended as limiting.

EXAMPLES

Example 1

N,N'-Dimethyl-2,3,5,6-tetraketopiperazine [Formula (1-1); $R^1=R^2=CH_3$] is an Active Material Used in Positive Electrodes; Discharge Tests Materials and Methods A positive electrode was prepared by mixing 45% by wt N,N'-dimethyl-2,3,5,6-tetraketopiperazine, 20% by wt acetylene black, and 35% by wt TAB-2. Note that TAB-2 is a commercial product purchased from Hohsen, Inc, as is acetylene black containing polytetrafluoroethylene as a binder. The above ingredients were mixed and pressed into a tablet having 120.9 mg and a diameter of 13 millimeters (mm).

A negative electrode was prepared from a lithium metal having a 13 mm diameter and a 0.38 mm thickness. An electrolyte solution was 130 μl of 1 mol/L LiPF$_6$ in propylene carbonate/dimethoxyethane (½), and a separator was Cellgard #2400 which was purchased from Hohsen, Inc. The components were combined as is well known in the art to produce a 2016 button type lithium battery.

FIG. 1 illustrates a cross-sectional view of one embodiment of a lithium battery in accordance to the present invention. A positive electrode can made of stainless steel 112, a current collector made of Ni mesh 106, a positive electrode 102, a separator 110, a negative electrode 104, a second current collector 108, a negative electrode can made of stainless steel 114 and a gasket 108 are shown.

Discharge tests on the Li battery were performed using a constant current of 300 μA and discharging the battery to 1.2 Volts. The discharge curve is shown in FIG. 2.

Results and Discussion

Figure 2:
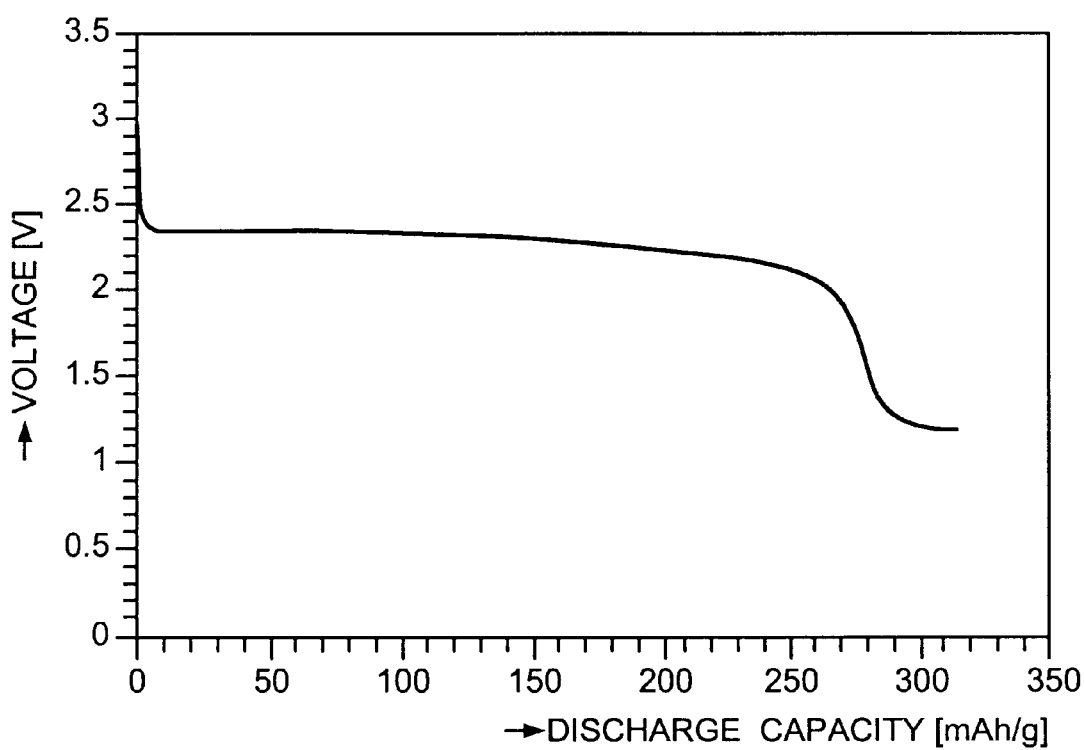
FIG. 2

As illustrated in FIG. 2, the lithium battery having N,N'-dimethyl-2,3,5,6-tetraketopiperazine as an active material for the positive electrode showed impressive flatness of discharge curve, electromotive force, discharge capacity, and discharge energy. In particular, the electromotive force was 3.2 V, the discharge capacity (till 1.3 V) was 289 mAh/g and the discharge energy (till 1.3 V) was 647 Wh/kg. Since the theoretical capacity is expected to be 315 mAh/g based on two electrons for a molecule, the effectiveness of the active material was 92%.

This data illustrates that the mono(tetraketopiperazine) compound represented by formula (1-1), a monomeric tetraketopiperazine unit-containing compound, is a new type of active material having high energy capacity and little adverse effect on the environment when disposed, and indicates that it is expected that it may be used in a number of applications as an active material or a component of active materials for batteries. The organic tetraketopiperazine compounds can be completely destroyed by an incinerator.

Example 2

A Thin Film of N,N'-dimethyl-2,3,5,6-tetraketopiperazine [Formula (1-1); R$^1$=R$^2$=CH$_3$] is an Active Material Used in Positive Electrodes: Discharge and Charge Tests Materials and Methods A thin film of positive electrode was prepared as follows: a mixture of 40% by wt N,N'-dimethyl-2,3,5,6-tetraketopiperazine, 40% by wt acetylene black, and 20% by wt poly(vinylidene fluoride) was well mixed with addition of a small amount of acetonitrile to give a slurry, which was coated to a thickness of approximately 50 μm onto a Ni mesh which was welded on a stainless steel support (diameter 14 mm×thickness 0.5 mm). The film was dried at 70° C. at atmospheric pressure for 1 hour, followed by room temperature under reduced pressure for 10 minutes. The weight of the thin film material coated on the support was 10.3 mg.

A negative electrode was prepared from a lithium metal having a 13 mm diameter and a 0.38 mm thickness. The electrolyte solution was a solution of 0.25 mol/L LiPF$_6$ in a 27:1:2 mixture of 1-butyl-3-methyl-1H-imidazolium hexafluorophosphate, propylene carbonate, and dimethoxyethane. The separator was Cellgard #2400 and a glass filter; these are set so that the Cellgard was attached on the positive electrode and the glass filter was attached on the lithium metal. The components were combined as is well known in the art to produce a 2016 button type lithium battery.

Discharge and charge tests on the Li battery were performed using a constant current of 117 μA. The battery was discharged to 2 V and charged up to 3V and repeated.

Results and Discussion

The first discharge capacity of the Li battery, having N,N'-dimethyl-2,3,5,6-tetraketopiperazine as an active material in the positive electrode, was 440 μAh and the tenth discharge capacity was 390 μAh.

This data illustrates that N,N'-dimethyl-2,3,5,6-tetraketopiperazine is an excellent rechargeable active material useful in thin film applications on positive electrodes. As above, this data indicates that mono(tetraketopiperazine) compound represented by formula (1-1), a monomeric tetraketopiperazine unit-containing compound, useful in rechargeable batteries and having little adverse effect on the environment when disposed, and that it is expected that it may be used in a number of applications as an active material or a component of active materials, including, both primary and secondary batteries.

Example 3

A Thin Film of Di(tetraketopiperazine) Compound Represented by Formula (1-2) [R$^1$=R$^2$=CH$_3$, A=(CH$_2$)$_2$] is an Active Material Used in Positive Electrodes: Discharge Tests Materials and Methods A thin film of positive electrode was prepared as follows: a mixture of 42.5% by wt di(tetraketopiperazine) compound represented by formula (1-2) wherein R$^1$=R$^2$=CH$_3$ and A=(CH$_2$)$_2$, 42.5% by wt acetylene black, and 15% by wt a 9:1 mixture of poly(vinylidene fluoride) and poly(methyl methacrylate) was well mixed with addition of a small amount of dichloromethane to give a slurry, which was coated to a thickness of approximately 10 μm onto a Ni mesh which was welded to a stainless steel support (diameter 14 mm×thickness 0.5 mm). The film was dried at room temperature for 1 hour under reduced pressure. The weight of the thin film material coated on the Ni mesh was 2.4 mg.

A negative electrode was prepared from a lithium metal having a 13 mm diameter and a 0.38 mm thickness. The electrolyte solution was a solution of 1 mol/L LiPF$_6$ in a 1:2 mixture of propylene carbonate and dimethoxyethane. The separator was composed of Cellgard #2400 and two glass filters, in which the Cellgard was between the glass filters. The components were combined as is well known in the art to produce a 2016 button type lithium battery. The battery was discharged at a constant current of 32 μA. The discharge curve is shown in FIG. 3.

Results and Discussion

Figure 3:
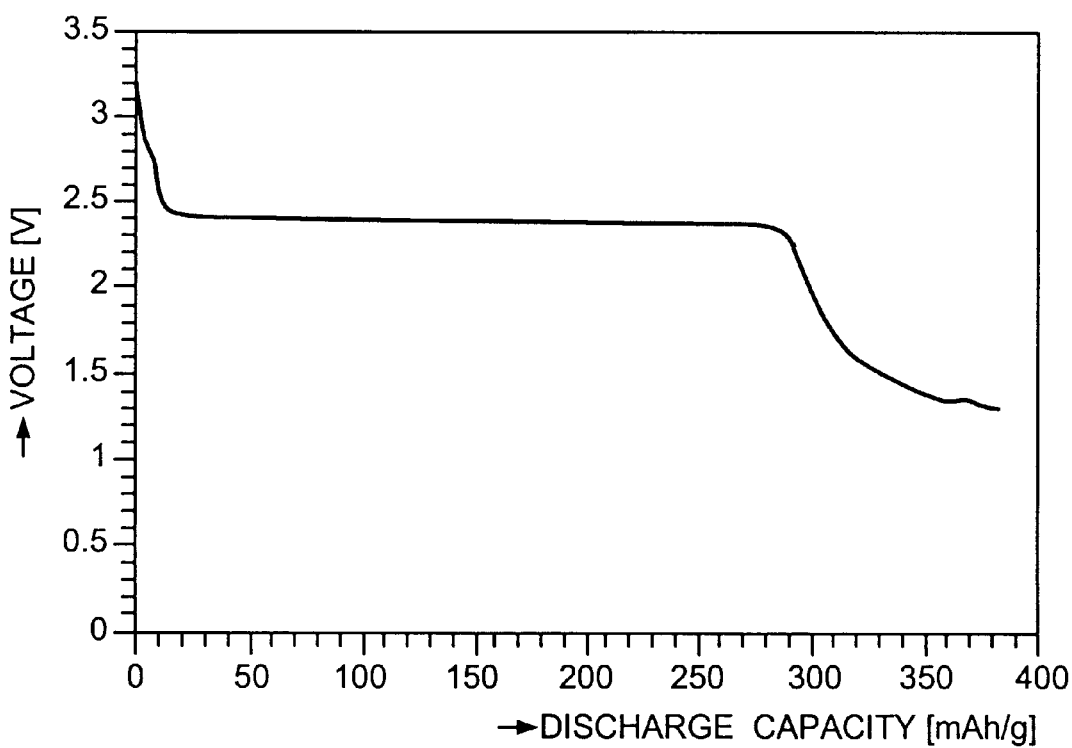
FIG. 3

As illustrated in FIG. 3, the lithium battery having the di(tetraketopiperazine) compound represented by formula (1-2), R$^1$=R$^2$=CH$_3$ and A=(CH$_2$)$_2$, as the active material for the positive electrode showed impressive discharge curve's flatness, electromotive force, discharge capacity, and discharge energy. In particular, the electromotive force (open circuit voltage) was 3.15V, the discharge capacity (till 2.0 V) was 300 mAh/g, the average voltage during the discharge was about 2.4V, and the discharge energy (till 2.0 V) was 725 Wh/kg. Since the theoretical capacity is expected to be 317 mAh/g based on four electrons for a molecule, the effectiveness of the active material was 95%.

This data illustrates that the di(tetraketopiperazine) compound represented by formula (1-2), a dimeric tetraketopiperazine unit-containing compound, is a new type of active material having high energy capacity and little adverse effect on the environment when disposed, and indicates that it is expected that it may be used in a number of applications as an active material or a component of active materials for batteries.

Example 4
A Thin Film of Di(tetraketopiperazine) Compound Represented by Formula (1-2) [$R^1=R^2=CH_3$, $A=(CH_2)_2$] is an Active Material Used in Positive Electrodes: Discharge and Charge Tests Materials and Methods A thin film of positive electrode was prepared as follows: a mixture of 42.5% by wt di(tetraketopiperazine) compound represented by formula (1-2) wherein $R^1=R^2=CH_3$ and $A=(CH_2)_2$, 42.5% by wt acetylene black, and 15% by wt a 9:1 mixture of poly(vinylidene fluoride) and poly(methyl methacrylate) was well mixed with addition of a small amount of dichloromethane to give a slurry, which was coated to a thickness of approximately 20 $\mu$m onto a Ni mesh which was welded to a stainless steel support (diameter 14 mm×thickness 0.5 mm). The film was dried at room temperature for 1 hour under reduced pressure. The weight of the thin film material coated on the Ni mesh was 4.2 mg.

A negative electrode was prepared from a lithium metal having a 13 mm diameter and a 0.38 mm thickness. The liquid electrolyte was a solution of 0.25 mol/L LiN$(SO_2CF_3)_2$ in 1-ethyl-3-methyl-1H-imidazolium bis(trifluoromethanesulfonyl)amide. The separator was composed of Cellgard #2400 and two glass filters, wherein the Cellgard was between the glass filters. The components were combined as is well known in the art to produce a 2016 button type lithium battery.

Discharge and discharge tests on the Li battery were performed. The battery was discharged to 2 V at a constant current of 57 $\mu$A and charged up to 3V at a constant current of 113 $\mu$A and repeated.

Results and Discussion

The first discharge capacity of the Li battery, having di(tetraketopiperazine) compound represented by formula (1-2), $R^1=R^2=CH_3$ and $A=(CH_2)_2$, as an active material in the positive electrode, was 132 $\mu$Ah and the twentieth discharge capacity was 117 $\mu$Ah.

This data illustrates that di(tetraketopiperazine) compound represented by formula (1-2) is an excellent rechargeable active material useful in thin film applications on positive electrodes. As above, this data indicates that di(tetraketopiperazine) compound represented by formula (1-2), a dimeric tetraketopiperazine unit-containing compound, useful in rechargeable batteries and having little adverse effect on the environment when disposed, and that it is expected that it may be used in a number of applications as an active material or a component of active materials, including, both primary and secondary batteries.

Example 5
A Thin Film of Di(tetraketopiperazine) Compound Represented by Formula (1-2) [$R^1=R^2=CH_3$, $A=(CH_2)_3$] is an Active Material Used in Positive Electrodes: Discharge Tests Materials and Methods A thin film of positive electrode was prepared as follows: a mixture of 42.5% by wt the di(tetraketopiperazine) compound represented by formula (1-2) wherein $R^1=R^2=CH_3$ and $A=(CH_2)_3$, 42.5% by wt acetylene black, and 15% by wt a 9:1 mixture of poly(vinylidene fluoride) and poly(methyl methacrylate) was well mixed with addition of a small amount of dichloromethane to give a slurry, which was coated to a thickness of approximately 20 $\mu$m onto a Ni mesh which was welded to a stainless steel support (diameter 14 mm×thickness 0.5 mm). The film was dried at room temperature for 1 hour under reduced pressure. The weight of the thin film material coated on the Ni mesh was 4.0 mg.

A negative electrode was prepared from a lithium metal having a 13 mm diameter and a 0.38 mm thickness. The electrolyte solution was a solution of 1 mol/L LiPF$_6$ in a 1:2 mixture of propylene carbonate and dimethoxyethane. The separator was composed of Cellgard #2400 and two glass filters, in which the Cellgard was between the glass filters. The components were combined as is well known in the art to produce a 2016 button type lithium battery. The battery was discharged at constant current of 52 $\mu$A.

Results and Discussion

The electromotive force (open circuit voltage) was 3.2V, the discharge capacity (till 2.0 V) was 276 mAh/g, the average voltage during the discharge was about 2.4V, and the discharge energy (till 2.0 V) was 665 Wh/kg. Since the theoretical capacity is expected to be 305 mAh/g based on four electrons for a molecule, the effectiveness of the active material was 90%.

This data illustrates that the di(tetraketopiperazine) compound represented by formula (1-2), a dimeric tetraketopiperazine unit-containing compound, is a new type of active material having high energy capacity and little adverse effect on the environment when disposed, and further indicates that it is expected that it can be used in a number of applications as an active material or a component of active materials for batteries.

Example 6
A Thin Film of Di(tetraketopiperazine) Compound Represented by Formula (1-2) [$R^1=R^2=CH_3$, $A=(CH_2)_4$] is an Active Material Used in Positive Electrodes: Discharge Tests Materials and Methods A thin film of positive electrode was prepared as follows: a mixture of 40% by wt, di(tetraketopiperazine) compound represented by formula (1-2) wherein $R^1=R^2=CH_3$ and $A=(CH_2)_4$, 40% by wt acetylene black, and 20% by wt poly(vinylidene fluoride) was well mixed with addition of a small amount of acetonitrile to give a slurry, which was coated to a thickness of approximately 25 $\mu$m onto a Ni mesh which was welded to a stainless steel support (diameter 14 mm×thickness 0.5 mm). The film was dried at 70° C. at atmospheric pressure for 1 hour. The weight of the thin film material coated on the Ni mesh was 5.1 mg.

A negative electrode was prepared from a lithium metal having a 13 mm diameter and a 0.38 mm thickness. The electrolyte solution was a solution of 1 mol/L LiPF$_6$ in a 1:2 mixture of propylene carbonate and dimethoxyethane. The separator was Cellgard #2400. The components were combined as is well known in the art to produce a 2016 button type lithium battery. The battery was discharged at a constant current of 60 $\mu$A.

Results and Discussion

The electromotive force (open circuit voltage) was 3.0V, the discharge capacity (till 2.0 V) was 242 mAh/g, the average voltage during the discharge was about 2.25V, and the discharge energy (till 2.0 V) was 534 Wh/kg. Since the theoretical capacity is expected to be 293 mAh/g based on four electrons for a molecule, the effectiveness of the active material was 83%.

This data illustrates that the di(tetraketopiperazine) compound represented by formula (1-2), a dimeric tetraketopiperazine unit-containing compound, is a new type of active material having high energy capacity and little adverse effect on the environment when disposed, and indicates that it is expected that it may be used in a number of applications as an active material or a component of active materials for batteries.

Example 7
A Thin Film of Di(tetraketopiperazine) Compound Represented by Formula (1-2) [$R^1=R^2=CH_3$, A=p-phenylene] is an Active Material Used in Positive Electrodes: Discharge Tests Materials and Methods A thin film of positive electrode was prepared as follows: a mixture of 42.5% by wt the di(tetraketopiperazine) compound represented by formula (1-2) wherein $R^1=R^2=CH_3$ and A=p-phenylene, 42.5% by wt acetylene black, and 15% by wt poly(vinylidene fluoride) was well mixed with addition of a small amount of N,N-dimethylformamide to give a slurry, which was coated to a thickness of approximately 12 μm onto a Ni mesh which was welded to a stainless steel support (diameter 14 m×thickness 0.5 mm). The film was dried at 60° C. for 30 minutes under reduced pressure. The weight of the thin film material coated on the Ni mesh was 2.4 mg.

A negative electrode was prepared from a lithium metal having a 13 mm diameter and a 0.38 mm thickness. The electrolyte solution was a solution of 1 mol/L $LiPF_6$ in a 1:2 mixture of propylene carbonate and dimethoxyethane. The separator was composed of Cellgard #2400 and two glass filters, in which the Cellgard was between the glass filters. The components were combined as is well known in the art to produce a 2016 button type lithium battery. The battery was discharged to 2 V at a constant current of 20 μA.

Results and Discussion

The electromotive force (open circuit voltage) was 3.3V, the discharge capacity was 263 mAh/g, the average voltage during the discharge was about 2.35V, and the discharge energy was 629 Wh/kg. Since the theoretical capacity is expected to be 278 mAh/g based on four electrons for a molecule, the effectiveness of the active material was 95%.

This data illustrates that the di(tetraketopiperazine) compound represented by formula (1-2), a dimeric tetraketopiperazine unit-containing compound, is a new type of active material having high energy capacity and little adverse effect on the environment when disposed, and indicates that it is expected that it may be used in a number of applications as an active material or a component of active materials for batteries.

Example 8
Preparation of N,N'-dimethyl-2,3,5,6-tetraketopiperazine [Formula (1-1); $R^1=R^2=CH_3$]
Method A; Yield of Tetraketopiperadine Compound is Dramatically Increased by Addition of Water Materials and Methods N,N'-Dimethyl-2,3,5,6-tetraketopiperazine prepared with no addition of water 3.3 g oxalyl chloride (0.026 mol) was added to a stirred solution of 2.33 g N,N'-dimethyloxamide (0.02 mol) in 20 mL of dry acetonitrile at 60° C. The mixture was stirred for 10 minutes at 60° C., and then heated to the reflux temperature of 76° C., and stirred for an additional 2 hours. The mixture was then cooled to 1° C. and the resultant precipitates were filtered. Precipitates were washed in succession with water, acetonitrile, and ether. The yield was 1.78 grams (52%) and the product identified by analysis of the NMR spectrum, IR spectrum, and Mass spectrum.

N,N'-Dimethyl-2,3,5,6-tetraketopiperazine prepared with addition of water 3.3 g oxalyl chloride (0.026 mol) was added to a stirred solution of 2.33 g N,N'-dimethyloxamide (0.02 mol) in 20 mL of dry acetonitrile at 60° C. The reaction mixture was stirred for 1 hour at 60° C. 0.72 ml water ($H_2O$) (0.04 mol) was drop wise added to the reaction mixture over a period of 15 minutes, followed by continued stirring for a 1.5 hours at 60° C. The mixture was then cooled to 1° C. and the resultant precipitates were filtered. Precipitates were washed with water, acetonitrile, and ether. The yield was 2.74 g (81%) and the product identified by analysis of the NMR spectrum, IR spectrum, and Mass spectrum, and the decomposition point.

Results and Discussion

The yield of the tetraketopiperazine prepared with addition of water was approximately 81%, a significant increase over the yield obtained from preparing the tetraketopiperazine with no addition of water, 52%. As shown in Table 1, the product prepared with addition of water showed the predicted decomposition point, NMR spectrum, IR spectrum, and Mass spectrum for uncontaminated tetraketopiperazine.

This data illustrates that preparation of mono (tetraketopiperizine) compound of formula (1-1)-with addition of water represents a significantly higher yield process than the previously utilized processes, and that the mono (tetraketopiperazine) compound was of high quality.

TABLE 1

| Type of Analysis | Result |
| --- | --- |
| Decomposition Point | ~380° C. |
| NMR Spectrum (ppm, DMF-d6) | 3.28 (singlet, $CH_3$) |
| IR Spectrum (KBr, $cm^{-1}$) | 1693 (C=O) |
| Mass Spectrum (m/e) | 142 ($M^+$—CO) |

Example 9
Preparation of N,N'-dimethyl-2,3,5,6-tetraketopiperazine [Formula (1-1), $R^1=R^2=CH_3$]
Method A; Yield of Tetraketopiperazine Compound is Dramatically Increased by Addition of Aqueous Alkali Solution Materials and Methods N,N'-Dimethyl-2,3,5,6-tetraketopiperazine was prepared with no addition of aqueous alkali solution as essentially described for the preparation of the tetraketopiperazine with no addition of water (Example 8).

N,N'-Dimethyl-2,3,5,6-tetraketopiperazine prepared with addition of an aqueous alkali solution 3.3 g oxalyl chloride (0.026 mol) was added to a stirred solution of 2.33 g N,N'-dimethyloxamide (0.02 mol) in 20 mL of dry acetonitrile at 60° C. The reaction mixture was stirred for 1 hour at 60° C. 0.29 mL 40% wt aqueous NaOH solution (NaOH: 0.004 mol, $H_2O$: 0.014 mol) was drop wise added to the reaction mixture, which was allowed to stir for an additional 1.5 hours at 60° C. The mixture was then cooled to 1° C. and the resultant precipitates were filtered. Precipitates were washed with water, acetonitrile, and ether. The yield was 2.55 g (75%) and the product identified by analysis of the NMR spectrum, IR spectrum, and Mass spectrum, and the decomposition point (see Table 1).

Results and Discussion

The yield of N,N'-dimethyl-2,3,5,6-tetraketopiperazine prepared with addition of aqueous alkali solution was approximately 75%, a significant increase over the yield obtained from preparing N,N'-dimethyl-2,3,5,6-tetraketopiperazine with no addition of aqueous alkali solution, 52%. The product, as in Example 1, showed the predicted decomposition point, NMR spectrum, IR spectrum, and Mass spectrum for uncontaminated N,N'-dimethyltetraketopiperazine.

This data illustrates that preparation of the tetraketopiperazine with addition of aqueous alkali solution represents a significantly higher yield process than the previously utilized processes, and that the resultant tetraketopiperazine was of high quality.

Example 10
Preparation of N,N'-diethyl-2,3,5,6-tetraketopiperazine [Formula (1-1), $R^1=R^2=C_2H_5$] Method A; N,N'-diethyl-2,3,5,6-tetraketopiperazine Prepared with Addition of Water 2.10 mL oxalyl chloride (0.024 mol) was added to a solution of 2.88 g N,N'-diethyloxamide (0.02 mol) in 40 mL of dry acetonitrile at 60° C. The reaction mixture was stirred for 1 hour at 60° C. and heated under reflux for 30 minutes. The reaction mixture was cooled to 60° C. and then 0.9 ml water (H$_2$O: 0.048 mol) was drop wise added to the reaction mixture, followed by continued stirring for a 1 hour at 60° C. The mixture was then cooled on an ice bath and the resultant precipitates were filtered. Precipitates were washed with acetonitrile, and ether to give 2.06 g of the product. The filtrate was concentrated to give additional amount (1.1 g) of the product. The total yield was 3.16 g (78%) of the product, which was identified to be N,N'-diethyl-2,3,5,6-tetraketopiperazine by analysis of the NMR spectrum, IR spectrum, and elemental analysis. The sample for the elemental analysis was recrystallized from acetonitrile. The physical and spectral data and elemental analysis data are shown below.

Melting point; 253–255° C.

NMR spectrum ($\delta$ in CD$_3$CN); 1.18 (t, J=7.3 Hz, CH$_3$, 6H), 3.88 (quartet, J=7.3 Hz, CH$_2$, 4H).

IR spectrum (KBr, cm$^{-1}$); 1702 (C=O).

Elemental analysis; Found: C, 48.53%, H; 5.00%, N; 14.27%. Calcd for C$_8$H$_{10}$N$_2$O$_4$: C, 48.48%, H; 5.09%, N; 14.14%.

Example 11
Preparation of 2,3,5,6-tetraketopiperazine [Formula (1-1), $R^1=R^2=H$]
Method B; Reaction of Oxalyl Halide and Silylamine 1.2 mol of oxalyl chloride was drop wise added to a stirred solution of 1.0 mol of hexamethyldisilazane in 1 L of 1,2-dichloroethane on an ice bath so that the temperature of the reaction mixture did not exceed 10° C. After the addition, the reaction mixture was heated to 70° C. and stirred at 70° C. for 16 hours. The reaction mixture was cooled to room temperature. The resulting precipitates were filtered, washed with ether, and dried to give 65.3 g (yield 92%) of 2,3,5,6-tetraketopiperazine as white precipitates, which was identified by the agreement of the spectral data with those reported in the literature [D. Ranganathan et al., *Journal of American Chemical Society*, Vol. 116, p.p. 6545–6557 (1994)]. The melting point of the product was more than 250° C.

Example 12
Preparation of N,N'-dimethyl-2,3,5,6-tetraketopiperazine [Formula (1-1), $R^1=R^2=CH_3$]
Method B; Reaction of Oxalyl Halide and Silylamine 30 mmol of oxalyl chloride was drop wise added to a stirred solution of 30 mmol of hexamethyldisilazane in 30 mL of 1,2-dichloroethane at 0° C. The reaction mixture was stirred at room temperature for 30 minutes and then at 80° C. for 16 hours. The resulting precipitates were filtered and washed with 1,2-dichloroethane and dried to give 16.5 mmol (yield 55%) of N,N'-dimethyl-2,3,5,6-tetraketopiperazine, spectral data of which were in agreement with those in Example 8. The data are shown in Example 8.

Example 13
Preparation of N-methyl-N'-phenyl-2,3,5,6-tetraketopiperazine [Formula (1-1); $R^1=CH_3$, $R^2=C_6H_5$]
Method C; Reaction of Oximidyl Halide and Amine 10.7 mmol of aniline was added to a stirred solution of 10.7 mmol of N-methyl oximidyl chloride [formula (5); $R^1=CH_3$, $X^1=X^2=Cl$] in 20 mL of dry acetonitrile at room temperature and the reaction mixture was heated under reflux for 2 hours. The reaction mixture was concentrated and the resulting precipitates were filtered to give 7.3 mmol (yield 68%) of the product, which was identified to be N-methyl-N'-phenyl-2,3,5,6-tetraketopiperazine [formula (1); $R^1=CH_3$, $R^2=$phenyl] by analysis of the NMR spectrum, IR spectrum, and elemental analysis. The sample for the elemental analysis was recrystallized from acetonitrile. The physical and spectral data and elemental analysis data are shown below.

Decomposition point; ~340° C.

NMR spectrum ($\delta$ in CD$_3$CN); 3.35 (s, CH$_3$, 3H), 7.26 (m, o-H, 2H), 7.56 (m, m-, p-H, 3H).

IR spectrum (KBr, cm$^{-1}$); 1703 (C=O), 1689 (C=O).

Elemental analysis; Found: C, 56.94%, H; 3.40%, N; 12.21%. Calcd for C$_{11}$H$_8$N$_2$O$_4$: C, 56.90%, H; 3.47%, N; 12.06%.

Example 14
Preparation of N-methyl-N'-(2'-nitrophenyl)-2,3,5,6-tetraketopiperazine [Formula (1-1); $R^1=CH_3$, $R^2=2\text{-}(NO_2)C_6H_4$]
Method D; Reaction of Oxalyl Halide and Silylamine, and Reaction with Amine Under a nitrogen atmosphere, a solution of 38.7 mmol of heptamethyldisilazane in 8.5 mL of dry dichloromethane was drop wise added to a stirred solution of 85.2 mmol of oxalyl chloride in 42.5 mL of dry dichloromethane at −20° C. The reaction mixture was gradually warmed to room temperature and stirred at the temperature for additional 30 minutes. The solvent, the excess of oxalyl chloride, and a byproduct (chlorotrimethylsilane) having a low boiling point were evaporated up from the reaction mixture. The remaining substance was dissolved in 72 mL of dry acetonitrile. Into the stirred acetonitrile solution, was added 36 mmol of 2-nitroaniline at room temperature. The reaction mixture was heated under reflux for 4 hours and cooled to room temperature. The solvent of the reaction mixture was evaporated and the residue was recrystallized from acetonitrile—ether to give 28.8 mmol (yield 80%) of the product as pale yellow crystals, which was identified to be N-methyl-N'-(2'-nitrophenyl)-2,3,5,6-tetraketopiperazine by analysis of the spectral data and elemental analysis data. The physical and spectral data and elemental analysis data are shown below.

Melting point with decomposition; 231–232° C.

NMR ($\delta$ in CD$_3$CN); 3.35 (s, CH$_3$, 3H), 7.53 (dd, J=1.4, 7.8 Hz, 6-H. 1H), 7.82 (dt, J=1.4, 7.8 Hz, 4-H, 1H), 7.93 (dt, J=1.4, 7.8 Hz, 5-H, 1H), 8.26 (dd, J=1.4, 7.8 Hz, 3-H, 1H).

IR spectrum (KBr, cm$^{-1}$); 1723 (C=O), 1694 (C=O), 1529 (NO$_2$), 1347 (NO$_2$).

Elemental analysis; Found: C, 47.58%, H; 2.64%, N; 15.33%. Calcd for C$_{11}$H$_7$N$_3$O$_6$: C, 47.66%, H; 2.55%, N; 15.16%.

Example 15
Preparation of N-methyl-N'-[3'-(acetylamino)phenyl]-2,3,5,6-tetraketopiperazine [Formula (1-1); $R^1=CH_3$, $R^2=3\text{-}(CH_3CONH)C_6H_4$]
Method D; Reaction of Oxalyl Halide and Silylamine, and Reaction with Amine Reactions of Example 15 were carried out in a similar manner as for Example 14 except that 3-(acetylamino)aniline was used in place of 2-nitroaniline and that the reaction mixture was heated under reflux for 16 hours in place of "heated under reflux for 4 hours". The reaction mixture's solvent was evaporated and the residue was washed with water, filtered, and dried. The yield of the product, N-methyl-N'-[3'-(acetylamino)phenyl]-2,3,5,6-tetraketopiperazine, was 73%. The physical and spectral data and elemental analysis of the product are shown below. The sample for the elemental analysis was recrystallized from acetonitrile.

Melting point with decomposition; 264–266° C.

NMR spectrum ($\delta$ in $CD_3CN$); 2.06 (s, $COCH_3$, 3H), 3.34 (s, $CH_3$, 3H), 6.94 (m, aromatic H, 1H), 7.48 (m, aromatic H, 2H), 7.77 (m, aromatic H, 1H), 8.50 (br.s, NH).

IR spectrum (KBr, $cm^{-1}$); 3561 (w), 3475 (w), 1706 (s) (C=O).

Elemental analysis; Found: C, 53.89%, H; 3.89%, N; 14.65%. Calcd for $C_{13}H_{12}N_5O_5$: C, 53.98%, H; 3.83%, N; 14.53%.

Example 16
Preparation of Di(tetraketopiperazine) Compound Represented by Formula (1-2) [$R^1=R^2=CH_3$, $A=(CH_2)_2$]
Method E; Reaction of Oxalyl Halide and Dioxamide 7.67 g (60 mmol) of oxalyl chloride was added to a stirred solution of 0.58 g (2.5 mmol) of dioxamide represented by formula (7), $R^1=R^2=CH_3$, $A=(CH_2)_2$, in 200 mL of dry acetonitrile at 60° C. and heated under reflux for 20 hours. 1.08 mL (0.06 mol) of water was drop wise added to the reaction mixture and the reaction mixture was continued to heat under reflux for additional 2 hours. The reaction mixture was cooled on an ice bath and the resulting precipitates were filtered, washed with acetonitrile, and dried to give 0.59 g (yield 70%) of the product, which was identified to be di(tetraketopiperazine) compound represented by formula (1-2), $R^1=R^2=CH_3$, $A=(CH_2)_2$, by analysis of the NMR spectrum, IR spectrum, and elemental analysis. The sample for the elemental analysis was further purified by washing with water, methanol, N,N-dimethylformamide, and then methanol. These data and physical data are shown below.

Decomposition point; ~370° C.

NMR spectrum ($\delta$ in $DMSO-d_6$); 3.19 (s, $CH_3$, 6H), 3.96 (s, $CH_2$, 4H).

IR spectrum (KBr, $cm^{-1}$); 1703 (C=O), 1685 (C=O).

Elemental analysis; Found: C, 42.56%, H; 2.94%, N; 16.57%. Calcd for $C_{12}H_{10}N_4O_8$: C, 42.61%, H; 2.98%, N; 16.56%.

Example 17
Preparation of Di(tetraketopiperazine) Compound Represented by Formula (1-2) [$R^1=R^2=CH_3$, $A=(CH_2)_2$]
Method F; Reaction of Oximiyl Halide and Diamine 2.6 mmol of 1,2-diaminoethane was added to a stirred solution of N-methyl oximidyl chloride [formula (5); $R^1=CH_3$, $X^1=X^2=Cl$] in 6 mL of dry acetonitrile at 0° C., and the reaction mixture was heated under reflux for 3 hours. The resulting precipitates were filtered and dried to give 1.43 mmol (yield 55%) of the tetraketopiperazine compound represented by formula (1-2), $R^1=R^2=CH_3$, $A=(CH_2)_2$, the spectral data of which were in agreement with those of the product obtained in Example 16. The data are shown in Example 16

Example 18
Preparation of Di(tetraketopiperazine) Compound Represented by Formula (1-2) [$R^1=R^2=CH_3$, $A=(CH_2)_3$]
Method G; Reaction of Oxalyl Halide and Silylamine, and Reaction with Diamine Under a nitrogen atmosphere, 66 mmol of hexamethyldisilazane was drop wise added to a stirred solution of 145 mmol of oxalyl chloride in 70 mL of dichoromethane at −20° C. and the reaction mixture was gradually warmed to room temperature. The solvent, the excess of oxalyl chloride, and a byproduct (chlorotrimethylsilane) having a low boiling point were evaporated up from the reaction mixture. The obtained substance was dissolved in 40 mL of dry acetonitrile. Into the stirred acetonitrile solution, was added 30 mmol of 1,3-diaminopropane at 0° C., and the reaction mixture was heated under reflux for 15 hours and poured to water. The resulting precipitates were filtered, washed with methanol, and dried to give 18.3 mmol (yield 61%) of the product, which was identified to be di(tetraketopiperazine) compound represented by formula (1-2), $R^1=R^2=CH_3$, $A=(CH_2)_3$, by analysis of the NMR spectrum, IR spectrum, and elemental analysis. The sample for the elemental analysis was further purified by recrystallizing from N,N-dimethylformamide; the obtained crystals were washed with methanol. These data and physical data are shown below.

Decomposition point; ~320° C.

NMR spectrum ($\delta$ in $DMF-d_7$); 1.97 (quintet, J=7.4 Hz, $CH_2$, 2H), 3.27 (s, $CH_3$, 6H), 3.97 (t, J=7.4 Hz, $NCH_2$, 4H).

IR spectrum (KBr, $cm^{-1}$); 1703 (C=O).

Elemental analysis; Found: C, 44.46%, H; 3.46%, N; 15.97%. Calcd for $C_{13}H_{12}N_4O_8$: C, 44.33%, H; 3.43%, N; 15.94%.

Example 19
Preparation of Di(tetraketopiperazine) Compound Represented by Formula (1-2) [$R^1=R^2=CH_3$, $A=(CH_2)_4$]
Method G; Reaction of Oxalyl Halide and Silylamine, and Reaction with Diamine The procedure and reaction were carried out in the same manner as in Example 18 except for 28.4 mmol of 1,4-diaminobutane in place of 30 mmol of 1,3-diaminopropane. As the result, 24.4 g (yield 86%) of the product was obtained, which was identified to be di(tetraketopiperazine) compound represented by formula (1-2), $R^1=R^2=CH_3$, $A=(CH_2)_4$, by analysis of the NMR spectrum, IR spectrum, and elemental analysis. The sample for the elemental analysis was further purified by washing with water, methanol, N,N-dimethylformamide, and then methanol. These data and physical data are shown below.

Decomposition point; ~350° C.

NMR spectrum ($\delta$ in $DMF-d_7$); 1.68 (m, $CH_2$, 4H), 3.28 (s, $CH_3$, 6H), 3.88 (m, $NCH_2$, 4H).

IR spectrum (KBr, $cm^{-1}$); 1703 (C=O).

Elemental analysis; Found: C, 45.96%, H; 4.03%, N; 15.53%.

Calcd for $C_{14}H_{14}N_4O_8$: C, 45.91%, H; 3.85%, N; 15.30%.

Example 20
Preparation of Di(tetraketopiperazine) Compound Represented by Formula (1-2) [$R^1=R^2=CH_3$, A=p-phenylene]
Method G; Reaction of Oxalyl Halide and Silylamine, and Reaction with Diamine Under a nitrogen atmosphere, 5.7 mmol of hexamethyldisilazane was drop wise added to 57 mmol of oxalyl chloride at room temperature with stirring and the reaction mixture was stirred for 1 hour. The excess of oxalyl chloride and a byproduct (chlorotrimethylsilane) having a low boiling point were evaporated up from the reaction mixture. The obtained substance was dissolved in 9 mL of dry acetonitrile. Into the stirred acetonitrile solution, was added 2.6 mmol of p-phenylenediamine at room temperature, and the reaction mixture was heated under reflux for 5 hours and cooled to room temperature. The resulting precipitates were filtered and dried to give 1.98 mmol (yield 76%) of the product, which was identified to be di(tetraketopiperazine) compound represented by formula (1-2), $R^1=R^2=CH_3$, A=p-phenylene, by analysis of the NMR spectrum, IR spectrum, and elemental analysis. The sample for the elemental analysis was further purified by washing with water, methanol, N,N-dimethylformamide, and then methanol. These data and physical data are shown below.

Decomposition point; ~340° C.

NMR spectrum ($\delta$ in DMSO-$d_6$); 3.28 (s, $CH_3$, 6H), 7.42 (s, aromatic H, 4H).

IR spectrum (KBr, $cm^{-1}$); 1716 (C=O), 1702 (C=O).

Elemental analysis; Found: C, 49.68%, H; 2.66%, N; 14.52%. Calcd for $C_{16}H_{11}N_4O_3$: C, 49.62%, H; 2.86%, N; 14.47%.

Example 21
Preparation of N-Methyl Oximidyl Chloride [Formula (5); $R^1=CH_3$, $X^1=X^2=Cl$]

Under a nitrogen atmosphere, a solution of 47.8 g (237 mmol) of hexamethyldisilazane in 60 mL of dichloromethane was drop wise added to a stirred solution of 76.2 g (600 mmol) of oxalyl chloride in 300 mL of dichloromethane at −20° C. for a period of 45 minutes. The reaction mixture was gradually warmed to −5° C. and then the reaction mixture was stirred on a water bath for additional 30 minutes. The solvent, the excess of oxalyl chloride, and a byproduct (chlorotrimethylsilane) having a low boiling point were evaporated up from the reaction mixture. The residue was dried in a vacuum to give 54.0 g (255 mmol; yield 93%) of very hygroscopic crystals, which was identified to be N-methyl oxamidoyl chloride [formula (5); $R^1=CH_3$, $X^1=X^2=Cl$] by the IR spectrum analysis: IR spectrum (KBr, $cm^{-1}$); 2956 (w) ($CH_3$), 1845 (s) (C=O of COCl), 1760 (s) (C=O of CON), 1436 (m), 1401 (s), 1287 (m), 1195 (s), 1127 (s), 1087 (m), 1049 (m), 1025 (m), 944 (s), 858 (s), 804 (m), 782 (s), 710 (m), 619 (m), 565 (m), 486 (s).

This product was used as a starting material in Examples 13 and 17, giving their respective final products, which were fully characterized by spectral and elemental analyses.

It will be clear that the invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

The entire disclosure and all publications cited herein are hereby incorporated by references.

What is claimed is:

1. A battery comprising:
a positive electrode wherein the positive electrode comprises a compound having at least one tetraketopiperazine-1,4-diyl unit represented by the formula:

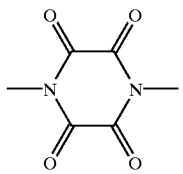

a negative electrode for generating electrons; and
an electrolyte disposed between the positive and negative electrodes, wherein the electrons generated at the negative electrode travel to the positive electrode to reduce the compound containing at least one tetraketopiperazine-1,4-diyl unit.

2. The battery of claim 1 further comprising a separator for electrically insulating the positive electrode from the negative electrode.

3. The battery of claim 1 wherein the positive electrode further comprises a binder.

4. The battery of claim 1 wherein the positive electrode further comprises an electroconductive agent.

5. The battery of claim 1 wherein the positive electrode further comprises a metal oxide, metal sulfide, or metal halide.

6. The battery of claim 1 wherein the positive electrode is in contact with a current collector.

7. The battery of claim 1 wherein the electrolyte is a liquid electrolyte.

8. The battery of claim 1 wherein the compound having at least one tetraketopiperazine-1,4-diyl unit is a polymeric, oligomeric, trimeric, dimeric, or monomeric compound.

9. The battery of claim 1 wherein the tetraketopiperazine-1,4-diyl unit content of the compound is 20% or more by weight.

10. The battery of claim 1 wherein the tetraketopiperazine-1,4-diyl unit content of the compound is 40% or more by weight.

11. The battery of claim 1 wherein the tetraketopiperazine-1,4-diyl unit content of the compound is 60% or more by weight.

12. The battery of claim 1 wherein the compound having at least one tetraketopiperazine-1,4-diyl unit is a compound having one tetraketopiperazine-1,4-diyl unit.

13. The battery of claim 12 wherein the compound having one tetraketopiperazine-1,4-diyl unit is a mono (tetraketopiperazine) compound represented by the formula:

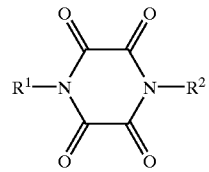

wherein $R^1$ and $R^2$ are independently a hydrogen atom or a substituted or unsubstituted alkyl or aryl group.

14. The battery of claim 13, wherein the alkyl group is an alkyl group having 1 to 10 carbon atoms which is unsubstituted or substituted with one or more substituents selected from the group consisting of a halogen atom, an aryl group, an alkoxy group, and an aryloxy group; and
wherein the aryl group is an aryl group having 6 to 10 carbon atoms which is unsubstituted or substituted with one or more substituents selected from the group consisting of an alkyl group, a halogen atom, an acyl group, a nitro group, a cyano group, an alkoxy group, an acylamino group, an alkylthio group, and an alkanesulfonyl group.

15. The battery of claim 14, wherein the alkyl group has 1 to 4 carbon atoms and the aryl group has 6 to 8 carbon atoms.

16. The battery of claim 13 wherein the mono (tetraketopiperazine) compound is N,N'-dimethyl-2,3,5,6-tetraketopiperazine.

17. The battery of claim 13 wherein the mono (tetraketopiperazine) compound is N,N'-diethyl-2,3,5,6-tetraketopiperazine.

18. The battery of claim 13 wherein the mono (tetraketopiperazine) compound is N-methyl-N'-phenyl-2,3,5,6-tetraketopiperazine.

19. The battery of claim 13 wherein the mono(tetraketopiperazine) compound is N-methyl-N'-(nitrophenyl)-2,3,5,6-tetraketopiperazine.

20. The battery of claim 13 wherein the mono(tetraketopiperazine) compound is N-methyl-N'-(acetylamino)phenyl-2,3,5,6-tetraketopiperazine.

21. The battery of claim 1 wherein the compound having at least one tetraketopiperazine-1,4-diyl unit is a compound having two tetraketopiperazine-1,4-diyl units.

22. The battery of claim 21 wherein the compound having two tetraketopiperazine-1,4-diyl units is a di(tetraketopiperazine) compound represented by the formula:

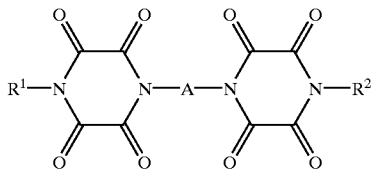

wherein $R^1$ and $R^2$ are independently a hydrogen atom or a substituted or unsubstituted alkyl or aryl group and A is a substituted or unsubstituted alkylene or arylene group.

23. The battery of claim 22 wherein the alkyl group is an alkyl group having 1 to 10 carbon atoms which is unsubstituted or substituted with one or more substituents selected from the group consisting of a halogen atom, an aryl group, an alkoxy group, and aryloxy group; and wherein the aryl group is an aryl group having 6 to 10 carbon atoms which is unsubstituted or substituted with one or more substituents selected from the group consisting of an alkyl group, a halogen atom, an acyl group, a nitro group, a cyano group, an alkoxy group, an acylamino group, an alkylthio group, and an alkanesulfonyl group; and wherein the alkylene group is an alkylene group having 1 to 10 carbon atoms which is unsubstituted or substituted with one or more substituents selected from the group consisting of an alkyl group, a halogen atom, an aryl group, an alkoxy group, and aryloxy group; and wherein the arylene group is an arylene group having 6 to 10 carbon atoms which is unsubstituted or substituted with one or more substituents selected from the group consisting of an alkyl group, a halogen atom, an acyl group, a nitro group, a cyano group, an alkoxy group, an acylamino group, an alkylthio group, and an alkanesulfonyl group.

24. The battery of claim 23, wherein the alkyl group has 1 to 4 carbon atoms, the aryl group has 6 to 8 carbon atoms, the alkylene group has 1 to 4 carbon atoms, and the arylene group has 6 to 8 carbon atoms.

25. The battery of claim 22 wherein the $R^1=R^2=CH_3$ and the $A=CH_2CH_2$.

26. The battery of claim 22 wherein the $R^1=R^2=CH_3$ and the $A=CH_2CH_2CH_2$.

27. The battery of claim 22 wherein the $R^1=R_2=CH_3$ and the $A=CH_2CH_2CH_2CH_2$.

28. The battery of claim 22 wherein the $R^1=R_2=CH_3$ and the A=phenylene.

* * * * *